United States Patent
Harding et al.

(10) Patent No.: US 11,905,547 B2
(45) Date of Patent: Feb. 20, 2024

(54) REAGENTS FOR ELECTROCHEMICAL TEST STRIPS

(71) Applicant: AgaMatrix, Inc., Salem, NH (US)

(72) Inventors: Ian Harding, Somerset (GB); Mary Y. Lee, Jamaica Plain, MA (US); Sandie Tan, Belmont, MA (US)

(73) Assignee: AgaMatrix, Inc., Salem, NH (US)

( * ) Notice: Subject to any disclaimer, the term of this patent is extended or adjusted under 35 U.S.C. 154(b) by 358 days.

(21) Appl. No.: 17/004,655

(22) Filed: Aug. 27, 2020

(65) Prior Publication Data

US 2020/0392556 A1 Dec. 17, 2020

Related U.S. Application Data

(63) Continuation of application No. 13/557,372, filed on Jul. 25, 2012, now Pat. No. 10,760,111.

(60) Provisional application No. 61/512,121, filed on Jul. 27, 2011.

(51) Int. Cl.
*G01N 33/52* (2006.01)
*C12Q 1/26* (2006.01)

(52) U.S. Cl.
CPC .............. *C12Q 1/26* (2013.01); *G01N 33/521* (2013.01)

(58) Field of Classification Search
CPC ....... A61K 31/167; C12Q 1/26; G01N 33/521
See application file for complete search history.

(56) References Cited

U.S. PATENT DOCUMENTS

| | | | |
|---|---|---|---|
| 3,950,133 A | 4/1976 | Monte et al. | |
| 3,997,470 A | 12/1976 | Monte et al. | |
| 4,225,410 A | 9/1980 | Pace | |
| 5,008,078 A | 4/1991 | Yaginuma et al. | |
| 5,120,420 A | 6/1992 | Nankai et al. | |
| 5,243,516 A | 9/1993 | White | |
| 5,288,636 A | 2/1994 | Pollmann et al. | |
| 5,352,351 A | 10/1994 | White et al. | |
| 5,378,628 A | 1/1995 | Gratzel et al. | |
| 5,393,903 A | 2/1995 | Gratzel et al. | |
| 5,410,059 A | 4/1995 | Fraser et al. | |
| 5,413,690 A | 5/1995 | Kost et al. | |
| 5,437,999 A | 8/1995 | Diebold et al. | |
| 5,508,171 A | 4/1996 | Walling et al. | |
| 5,589,326 A | 12/1996 | Deng et al. | |
| 5,708,247 A | 1/1998 | McAleer et al. | |
| 5,846,702 A | 12/1998 | Deng et al. | |
| 5,858,695 A | 1/1999 | Kadota et al. | |
| 5,942,102 A | 8/1999 | Hodges et al. | |
| 6,187,751 B1 | 2/2001 | Smith et al. | |
| 6,258,229 B1 | 7/2001 | Winarta et al. | |
| 6,258,254 B1 | 7/2001 | Miyamoto et al. | |
| 6,284,125 B1 | 9/2001 | Hughes et al. | |
| 6,605,201 B1 | 8/2003 | Mao et al. | |
| 6,676,816 B2 | 1/2004 | Mao et al. | |
| 7,074,308 B2 | 7/2006 | Mao et al. | |
| 7,090,756 B2 | 8/2006 | Mao et al. | |
| 7,135,100 B1 | 11/2006 | Lau et al. | |
| 7,169,273 B2 | 1/2007 | Ikura et al. | |
| 7,501,052 B2 | 3/2009 | Iyengar et al. | |
| 7,582,123 B2 | 9/2009 | Fadli et al. | |
| 7,608,180 B2 | 10/2009 | Lau et al. | |
| 7,749,766 B2 | 7/2010 | Pei et al. | |
| 7,816,145 B2 | 10/2010 | Nakaminami et al. | |
| 8,741,491 B2 * | 6/2014 | Wolfe .................. | C07D 487/08 548/335.1 |
| 2005/0258036 A1 | 11/2005 | Harding | |
| 2005/0265094 A1 | 12/2005 | Harding et al. | |
| 2006/0096859 A1 | 5/2006 | Lau et al. | |
| 2007/0295616 A1 | 12/2007 | Harding et al. | |
| 2009/0295616 A1 | 12/2009 | Martin | |
| 2010/0025265 A1 | 2/2010 | Hsiung et al. | |
| 2010/0270175 A1 | 10/2010 | Pei et al. | |
| 2013/0092536 A1 | 4/2013 | Carrington et al. | |

FOREIGN PATENT DOCUMENTS

| | | |
|---|---|---|
| EP | 0012035 A1 | 6/1980 |
| EP | 0213279 A2 | 3/1987 |
| EP | 0770688 A1 | 5/1997 |
| EP | 2224018 A1 | 9/2010 |
| WO | 9013634 A2 | 11/1990 |
| WO | 9700441 A1 | 1/1997 |
| WO | 0100865 A2 | 1/2001 |
| WO | 2012173694 A1 | 12/2012 |

OTHER PUBLICATIONS

Cheng et al., Determination of stepwise stability constants for aqueous hexacyanoferrate-tetramethylammonium ions pairs by cyclic voltammetry, Analytica Chimica Acta, 1991, pp. 35-38, vol. 251, No. 1-2, Elsevier, Amsterdam, NL.

De Mattos, I. L. et al., Development of biosensors based on hexacyanoerrates, Talanta, 2000, pp. 791-799, vol. 52, No. 5 XP55036941.

Eaton et al., Thermodynamic aspects of the potassium hexacyanoferrate(III)-(II) system. I. Ion association, The Journal of Physical Chemistry, 1967, pp. 2016-2021, vol. 71, No. 7, Publication Date (Web) May 1, 2002, http://pubs.acs.org.

(Continued)

*Primary Examiner* — Gurpreet Kaur
(74) *Attorney, Agent, or Firm* — Larson & Anderson, LLC

(57) ABSTRACT

A dry reagent composition that includes an active redox enzyme that oxidizes an analyte as a specific substrate to produce an inactive reduced form of the enzyme; and a salt of ferricyanide provides improved performance in electrochemical test strips such as those used for detection of glucose. The salt of ferricyanide consists of ferricyanide and positively-charged counter ions, and the positively charged counter ions are selected such that the salt of ferricyanide is soluble in water, and such that the salt of ferricyanide or the crystalline phase of the salt of ferricyanide has a solubility in water and/or a lower $E^0_{\mathit{eff}}$ at a concentration of 100 mM than potassium ferricyanide. For example, the salt of ferricyanide may be tetramethylammonium ferricyanide.

16 Claims, 13 Drawing Sheets

(56) References Cited

OTHER PUBLICATIONS

Good et al., Hydrogen Ion Buffers for Biological Research, Biochemistry, 1966, pp. 467-477, vol. 5, No. 2.

Hanania et al., Thermodynamic aspects of the potassium hexacyanoferrate(III)-(II) system. II. Reduction potential, The Journal of Physical Chemistry, 1967, pp. 2022-2030, vol. 71, No. 7, Publication Date (Web) May 1, 2002, http:/pubs.acs.org.

Jiang M. et al., Preparation and characterization of mixed-valent titanium hexacyanoferrate film modified glassy carbon electrode, Journal of Electroanalytical Chemistry and Interfacial Electro Chemistry, 1990, pp. 289-296, vol. 292, No. 1-2 Publisher: Elsevier, Amsterdam, NL.

Taha, M. et al., New Insights into Buffer-Ionic Salt Interactions: Solubilities, Transfer Gibbs Energies, and Transfer Molar Volumes of TAPS and TAPSO from Water to Aqueous Electrolyte Solutions, J Solution Chem, 2010, pp. 1665-1680, vol. 39.

Talbott, J. et al., A New Microchemical Approach to Amperometric Analysis, Microchemical Journal, New York, NY, 1998, pp. 5-12, vol. 37, No. 1; XP000991141.

\* cited by examiner

REAGENTS FOR ELECTROCHEMICAL TEST STRIPS

BACKGROUND OF THE INVENTION

This application relates to reagents for electrochemical test strips such as the type commonly used in detection of blood glucose, and to compositions, test strips and related methods making use of such reagents.

A large fraction of biosensors, measured both by commercial value and academic interest, involve harnessing the specificity of an oxidoreductase enzyme towards a specific molecule (or "analyte") of interest. The oxidoreductase enzyme in these biosensors is used to catalyze the transfer of electrons off the specific molecule of interest and onto a chemical that is more readily detectable by some transduction mechanism, or vice versa. Transduction mechanisms include measuring concentrations by electrochemical, electrical or optical means. Chemicals that are more readily detectable by these transduction mechanisms are called "mediators" because of their intermediary role between the biological enzyme and the sensing mechanism in the biosensor.

A subset of the oxidoreductase enzymes are the oxidases, which use oxygen already present in a sample as a mediator, often forming hydrogen peroxide as the moiety which has accepted the electrons from the enzyme. Biosensors based on detection of hydrogen peroxide formed an early generation of devices but these were commercially hampered by the difficulty of detecting the peroxide, which is electrochemically detectable only at a catalytic electrode such as platinum.

Several methods to overcome this difficulty were developed. Of some relevance to this invention are the disclosures of Lau et al (U.S. Pat. Nos. 7,135,100 and 7,608,180) where different salts of ferricyanide were used to facilitate transfer of electrons off the hydrogen peroxide (formed when oxygen acts a mediator to regenerate enzyme) and into the electrode. Thus, the ferricyanide in this system does not act as a mediator with respect to the enzyme, but rather acts at one step removed from the enzyme. The salts of Lau are chosen for their solubility in organic solvents and polymers and low solubility in water, which is a criterion aimed at tackling another difficulty with peroxide-mediated biosensors. This is that the analyte of interest is often in a biological sample in the presence of catalase, which decomposes peroxide without release of the electrons. Methods such as the use of membranes had to be developed in biosensors to keep the catalase away from the peroxide generated and membrane-soluble ferricyanides developed so that the signal could reach the electrode and be detected.

Another response to the problems of these peroxide-based biosensors was the development of reagent systems for biosensors based on oxidase enzymes that could operate without the need for oxygen mediation. Such systems commonly used potassium ferricyanide as a direct mediator to restore enzyme to an active state. Salts of ferricyanide other than the potassium salt have been mentioned in combination with oxidoreductase enzymes before and include: 'sodium ferricyanide' (as in U.S. Pat. Nos. 7,816,145, 7,749,766, 7,582,123, 7,169,273, 6,258,254) or 'an alkali metal ferricyanide (e.g., potassium or sodium ferricyanide)' U.S. Pat. No. 6,187,751. In three other examples, salts of ferricyanide are listed indiscriminately: 'the metal ion includes, for example, alkali metal ion such as lithium, sodium, and potassium ion; alkaline earth metal ion such as magnesium and calcium ion; and also aluminium and zinc ion' (Kadota et al U.S. Pat. No. 5,858,695) or targeted towards a solubility in organic solvents (Lau et al U.S. Pat. Nos. 7,135,100 and 7,608,180 mentioned above).

Potassium ferricyanide is a good mediator for a variety of oxidoreductase enzymes. Even for oxidase enzymes such as glucose oxidase, potassium ferricyanide at high concentrations (~100 mM or greater) is a sufficiently fast mediator that it can mostly outcompete the less concentrated oxygen in a sample, which then becomes only an interferent. The solubility of potassium ferricyanide in water gives another advantage of biosensor formulations that contain it; when ferricyanide is present in large amounts (for example, Walling et al in U.S. Pat. No. 5,508,171 define a useful range for potassium ferricyanide 'from about 0.15 molar (M) to about 0.7 M' in their sensor) it can support an adequate counter reaction at the counter electrode to balance the reaction at the working electrode. The counter reaction provides sufficient current and anchors the chemical potential so that no reference electrode is needed nor is it necessary for the counter electrode to be larger than the working electrode. This means sensors can be simplified to two-electrode sensors with electrodes of the same size and material. Other work using this type of reagent is found in WO 97/00441, U.S. Pat. Nos. 5,708,247 and 6,258,229.

However, and perhaps as a consequence of its widespread use, problems with potassium ferricyanide are widely recognized. These include sensitivity to oxygen because even if the ferricyanide can out-compete the oxygen as a mediator, the ferrocyanide produced is still susceptible to oxidation by oxygen. Another problem of ferricyanide is the tendency for some of the ferricyanide to transform into ferrocyanide, even in a dried reagent over a prolonged period, if the potassium ferricyanide is left in intimate contact with the enzyme. Various methods of creating formulations have been disclosed to ameliorate this problem: Nankai et al (U.S. Pat. No. 5,120,420) deposit their enzyme and potassium ferricyanide in layers separated by a 'hydrophilic high molecular substance layer' to keep them apart and ensure 'excellent preservation properties,' while Walling et al (U.S. Pat. No. 5,508,171) use a microcrystalline cellulose to disperse the potassium ferricyanide.

With the increase in emphasis for faster test times and improved accuracy, the slow mediation rate of potassium ferricyanide (requiring higher concentrations) and its tendency to produce ferrocyanide in the dried reagent mean the ferricyanide ion is falling out of favour as a component in biosensor reagents. To this end, mediators have been developed that do not need such high concentrations to outcompete oxygen e.g. the metal bipyridyl ("bpy") complexes of U.S. Pat. Nos. 5,378,628, 5,393,903, 5,437,999, 5,410,059, 5,589,326, 5,846,702, metal pyridyl-imidazole complexes of U.S. Pat. Nos. 6,605,201, 6,676,816, 7,074,308 and the bidentate imidazole complexes of U.S. Pat. No. 7,090,756. These types of complex, however do not always have the high solubilities to support the necessary counter reaction and so the strip construction has to be more complex, with the introduction of a reference or Ag/AgCl counter/reference electrode. Types of high-solubility Os complexes have been described in U.S. Pat. No. 5,589,326 but the cost of osmium complexes makes this approach markedly more expensive than potassium ferricyanide for disposable strips.

It is possible to supplement the activity of potassium ferricyanide by adding a second mediator, including those described above; this generally results in the problem of accentuating the worst features of both mediators, in particular: (a) the oxidation potential required must suit the highest mediator oxidation potential, (b) the loss of signal due to oxygen will be dominated by the worst of the two mediators in this respect, and (c) the size of the signal will only be that of the best performing mediator. Furthermore, the addition of a second mediator to a formulation containing potassium ferricyanide accentuates the production of ferrocyanide in the dried reagent. Methods around these problems have to be developed and these include Guo et al's method of physical separation of reagent components on two electrodes in a sandwich (U.S. Pat. No. 6,033,866).

A partial solution to the problem is presented by Harding et al, US 2007/0295616-A1, which is incorporated herein by reference, where careful selection of electrode potentials allows two electron-transfer species to act in concert rather than in parallel. In this system, a mediator regenerates the enzyme, and a shuttle compound serves as the primary or even the only electroactive species for transfer of electrons to and from the electrodes. Specific combinations of mediator and shuttle compounds disclosed in the application include $[Os(MeBpy)_2(Im)_2]^{2+/3+}$ or $[Os(Mebpy)_2Pic]^{+/2+}$ as mediators and ferri/ferrocyanide as the shuttle. U.S. Pat. No. 5,508,171, which is incorporated herein by reference, also discloses some systems in which two mediators are employed.

SUMMARY OF THE INVENTION

The present application provides solutions to many of the problems associated with potassium ferricyanide mediators including in particular the shelf stability of test strips containing the reagent through the use of carefully selected ferricyanide salts. Thus, in a first aspect, the present application relates to a dry reagent composition comprising:

(a) an active redox enzyme that oxidizes/reduces an analyte as a specific substrate to produce an inactive form of the enzyme; and (b) a salt of ferricyanide, wherein the salt of ferricyanide consists of ferricyanide and positively charged counter ions, said positively charged counter ions being selected such that the salt of ferricyanide is soluble in water to at least twice the maximum analytical concentration of the analyte in the sample but less than the solubility of potassium ferricyanide and/or such that the ferricyanide salt has a lower $E^0_{\mathit{eff}}$ at a concentration of 100 mM that is less than that of 100 mM potassium ferricyanide.

The $E^0_{\mathit{eff}}$ can be measured for the entirety of the salt of ferricyanide, or for just the crystalline phase thereof. Exemplary salts of ferricyanide are rubidium ferricyanide and tetramethylammonium ferricyanide.

The "maximum analytical concentration" is the upper end of the designed dynamic range for a given sensor. In the case of blood glucose, this value is commonly 600 mg/dL.

The dry reagent may also contain additional electron transfer mediator(s), buffering agents and wetting agents. In preferred embodiments, cations associated with such additional agents are at least mainly the same, and preferably all the same as the positively charged counter ion of the salt of ferricyanide.

The invention further relates to electrochemical test strips that comprise metal electrodes and the dry reagent composition of the invention. This dry reagent of the invention substantially and surprisingly increases the shelf life of the electrochemical test strip prior to application of sample without impairing the quality of the test results obtained. In accordance with this aspect of the invention, electrochemical test strips for detection of an oxidizable analyte such as glucose in a sample, comprise:

(a) first and second non-reactive electrodes;

(b) a sample cell for receiving a liquid sample, wherein a liquid sample disposed within the sample cell is in contact with the first and second electrodes; and (c) a dry reagent in accordance with the invention.

The dry reagent is disposed such that upon application of a liquid sample to the test strip the dry reagent dissolves in the sample within the sample cell.

The invention also provides a liquid composition comprising the reagent of the invention in an aqueous liquid carrier. Such a liquid composition is obtained when a liquid sample such as blood is introduced into a sample chamber of a test strip, or when a liquid carrier is mixed with a reagent prior to application to the test strip. Such a composition may also be used during manufacturing to deliver reagent composition to a test device, prior to subsequent drying for storage and distribution.

The invention also provides a method for detecting analyte in a liquid sample by applying the sample to a test strip of the invention, wherein the enzyme in the dried reagent is selected to be specific for the analyte; and then applying an external signal to the test strip to generate a signal indicative of the amount of analyte in the sample. In specific embodiments, the external signal is a potential applied between the first and second electrodes, and the signal indicative of the amount of analyte is a current.

The invention also provides a method for formulating a shelf stable reagent for use in electrochemical detection of an analyte. The method comprises the steps of (a) selecting an oxidoreductase enzyme that oxidizes/reduces the analyte as a specific substrate;

(b) selecting a salt of ferricyanide, wherein the salt of ferricyanide consists of ferricyanide and selected positively charged counter ions, said positively charged counter ions being selected such that the salt of ferricyanide is soluble in water, and the salt of ferricyanide or the crystalline phase of the ferricyanide salt has a solubility in water at least twice the maximum analytical concentration of the analyte in the sample but less than the solubility of potassium ferricyanide and/or such that the ferricyanide salt has a lower $E^0_{\mathit{eff}}$ at a concentration of 100 mM that is less than that of 100 mM potassium ferricyanide; and (c) combining the selected enzyme and the selected salt of ferricyanide to form a shelf stable electrochemical test reagent for use in detection of the analyte.

DETAILED DESCRIPTION OF THE INVENTION

Figure 1:
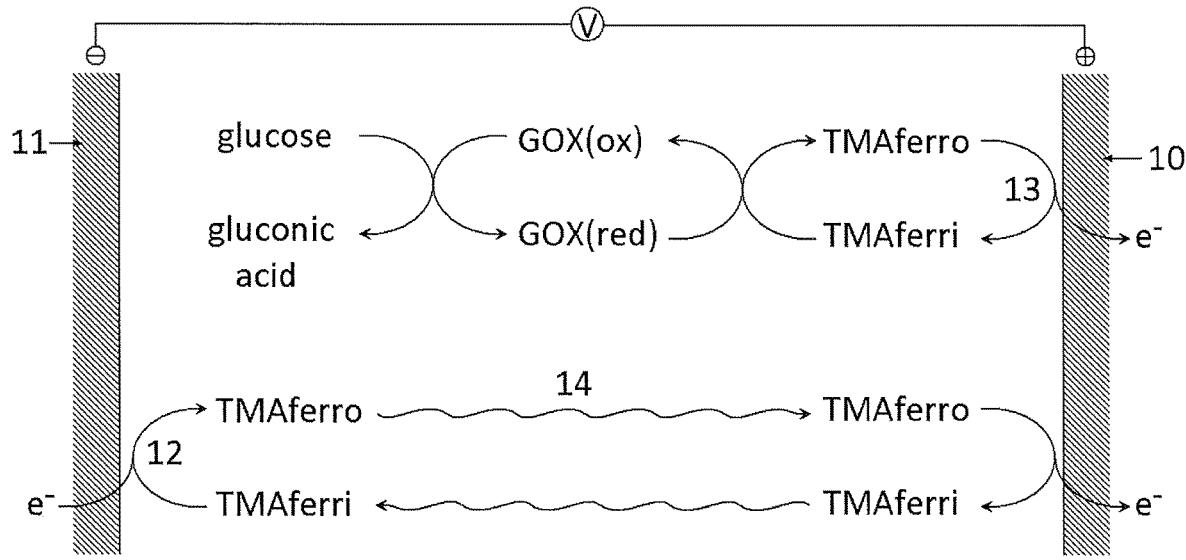
FIG. 1 shows a set of reactions occurring in a test strip containing a dry reagent in accordance with a first embodiment of the invention when a sufficient potential is applied to the electrodes.

The present application relates to a reagent composition and to electrochemical test strips that include this composition for use in the detection of an analyte.

Definitions

As used in the specification and claims of this application, the following definitions of terms are applicable:

In general, the term "analyte" refers to a substance of interest in a sample, of which the presence or amount is to be determined. In the case of the present application, the term analyte refers specifically to a compound that (a) is not directly oxidizable or reducible at a metal or other non-reactive electrode in aqueous solution, at a potential difference of less than 1 V; and (b) is directly oxidizable or reducible by a redox enzyme in aqueous solution. Various analytes that meet these characteristics have been disclosed for detection by "biosensors" including, without limitation glucose, cholesterol, and those other analytes listed in Table 1. While the examples in this application refer to glucose, which is a preferred analyte, other analytes and corresponding enzymes may be substituted without departing from the scope of the present invention, and any example or structure in which glucose is employed is completely applicable to other analytes with appropriate changes in enzyme and electroactive species.

The term "active redox enzyme' refers to an enzyme that is in a redox state that allows it to oxidize or reduce a selected analyte as a specific substrate. This oxidation or reduction produces an inactive form of the enzyme which can no longer perform this function. In any given reagent in accordance with the invention, the enzyme will be selected to have the desired analyte as a specific substrate. Examples of analyte/enzyme pairs are listed in Table 1 which is based in part on Table I of U.S. Pat. No. 4,225,410, which is incorporated herein by reference.

The term "electron transfer mediator" refers to a chemical compound that has the ability to regenerate active redox enzyme from inactive enzyme formed by reaction with the analyte. The electron transfer mediator must have an electrochemical potential sufficient to oxidize or reduce the inactive form of the enzyme to regenerate the active form in a sample applied to a test strip (commonly an aqueous medium such as blood, urine or saliva). Thus, the analyte that is of interest controls the selection of enzyme, and the enzyme controls the selection of the electron transfer mediator in the reagent.

The term "test strip" refers to an assemblage of parts that includes electrodes and a reagent appropriate for the electrochemical detection of at least one analyte, and a connector for attachment of the strip to a meter. The test strip may have multiple electrode sets and reagents for multiple analytes, or for multiple determinations of the same analyte. In specific embodiments, the test strip is a single use, disposable element.

The term "meter" refers to an electronic device that associates with a test strip to provide an integrated test unit for determination of one or more analytes in a sample when the sample is applied to a test strip associated with a meter. In general, the meter applies potential to the test strip to stimulate the electrochemical reactions, and detects and analyzes the resulting signals. However, the meter could perform only part of these functions, for example application of potential and detection of signal, with analysis being performed in a separate component.

The terms "TMA ferri," "TMA ferro," and "TMA couple" refer, respectively, to tetramethylammonium ferricyanide, tetramethylammonium ferrocyanide, and to the combination of TMA ferri and TMA ferro in a common solution as a redox couple.

The term "sufficient potential" refers to a potential difference between electrodes which is large enough to result in the oxidation and reduction of the ferricyanide couple (for example a TMA couple) at the electrodes. A voltage may be applied to one or both electrodes to create the potential difference between the electrodes.

The term "solubility" refers to the amount of a compound that can be dissolved in water. It can be expressed in a variety of ways (e.g., mass of compound per mass of water, mass of compound per volume of water, defined in actual units or expressed as a % value) but the most valuable unit for comparison in this disclosure, at least for the ferricyanide salts, is in moles of compound per liter (Molar, M) since this allows direct comparison of the ferricyanide content. Solubilities of ferricyanide salts are appropriately compared at conventional temperatures that would be associated with the storage and use of the strip, for example 25° C.

The term "soluble in water" when applied to the ferricyanide salts used in the invention indicates a degree of solubility sufficient to achieve concentrations in an aqueous sample, such as blood, that are suitable for performing an electrochemical assay. For most purposes, this means a solubility sufficient to achieve concentrations of at least 80 mM, although the actual concentration in an operating test strip device need not be this high. The lower limit of solubility is set by the concentration of oxidized mediator that is necessary at the negative electrode to ensure that current is limited by the concentration of reduced species at the positive electrode; this limit depends on the amount of reduced species generated by the maximum concentration of analyte. For glucose, glucose oxidoreductases typically catalyse oxidation of only the beta-D-glucose, which is 64% of the total glucose, and generate 2 moles of ferrocyanide per mole of glucose, so for a maximum analytical blood glucose concentration of 600 mg/dL (i.e., 33.3 millimolar (mM)) 42.7 mM ferrocyanide will be generated. At least twice this concentration of ferricyanide (i.e., 85.4 mM) is desirable in the reagent to have an excess left over after forming ferrocyanide so that the oxidation of ferrocyanide at the positive electrode remains current limiting. For potassium ferricyanide, this would correspond to a solubility of at least 28.1 g/L and for compounds with cations of higher weight than potassium it is even greater. In contrast, U.S. Pat. No. 7,135,100 indicates that the compounds with low water-solubility have a maximum solubility of 20 g/L.

The term "$E^0_{eff}$" refers to an electrode potential for a given electroactive species at the concentration of interest and in the presence of ions of interest. The electrode potential of ferricyanide is an expression of the equilibrium represented by the following chemical half-reaction:

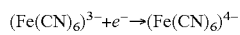

$(Fe(CN)_6)^{3-} + e^- \rightarrow (Fe(CN)_6)^{4-}$

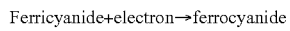

Ferricyanide+electron→ferrocyanide

Electrochemists recognize that the standard electrode potential $E^0$ can be used in equations like the Nernst equation to determine the ratio of the two chemical species at any particular chemical potential, E:

$$E = E^0 + (RT/nF) \ln\{[\text{ferri}]/[\text{ferro}]\}$$

where R is the gas constant, T the absolute temperature (in Kelvin), n the number of electrons transferred in the half reaction (which is 1 for ferricyanide), F is Faraday's constant, [ferri] is the concentration of the ferricyanide ion, $(Fe(CN)_6)^{3-}$, and [ferro] is the concentration of the ferrocyanide ion, $(Fe(CN)_6)^{4-}$. This equation sets the expectation that chemical potential, E, is independent of the nature of the cations in the system and that the standard electrode potential, $E^0$, can be determined from the chemical potential of a solution where [ferri]=[ferro]. The converse is also expected, that $E^0$ can be used to predict other concentration ratios from measurements of the electrode potential or, conversely, to predict electrode potentials from ratios of [ferri]/[ferro]. However, electrochemists also recognize that at increasing concentrations, direct use of concentration values leads to errors and that these should be substituted by thermodynamic activities.

Beyond the ideal Nernst equation, research by Hanania et al (J. Phys Chem 1967, 71, pp 2022-2030) has explored the idea that the ferricyanide and ferrocyanide ions form complexes or ion pairs with cations in solution. This work has set the commonly used data-book value of $E^0$=356 mV vs the standard hydrogen electrode, which is the limit at infinite dilution, but also has explored the equilibria that exist between higher concentrations of potassium ions, ferricyanide and ferrocyanide in detail. In addition, the influence of other salts (alkali metal and tetraalkylammonium salts) on the electrode potential has also been briefly explored. Hanania et al report that although the tetraalkylammonium ferricyanide salts give lower electrode potentials, addition of "neutral salts like KBr and NaCl . . . give an immediate dramatic rise in the reduction potential". Thus, any determination of $E^0$ will depend not just on the concentrations but also on the particular complexes that may be present. The term $E^0_{eff}$ is a form of $E^0$ that is applicable for the particular salt at a particular total concentration of reduced and oxidized species.

In the dry reagent of the invention, when additional salts that include a cationic counter ion are present in the reagent, it is preferred that this cationic counter ion be at least mainly the same as the positively-charged counter ion in ferricyanide salt employed. The term "mainly the same" means that in the dry reagent as a whole, less than 25% of the positively-charged counter ions are different from the counter ion of the ferricyanide. It will be appreciated that an additional material may have substantially all of its counter ions different if the amount of additional material employed is small relative to the amount of the salt of ferricyanide on a molar basis, and that the importance of keeping the counter ions the same increases as the relative amount of additional material increases. In specific embodiments, less than 10%, and more preferably less than 5% of the positively-charged counter ions are different from the counter ion of the ferricyanide.

In some embodiments, "essentially all" of the cationic counter ions associated with additional materials are the same as the positively-charged counter ion in the ferricyanide salt employed. As used in this context, the term "essentially all" does not require that there are no other detectable counter ions, but that any such counter ions would be considered impurities in the additional material added. In specific embodiments, the purity of the additional material is a salt that has at least 98% purity for the compound including the counter ion that is the same as positively-charged counter ion in the salt of ferricyanide.

The term "shelf-stable reagent" refers to a dry reagent that, when in contact with gold electrodes has a shelf life that is greater than that of otherwise identical composition in which potassium ferricyanide is used as the ferricyanide component under identical conditions. Shelf life may be evaluated using accelerated aging techniques and measured on the basis of a comparison of results achieved with a glucose containing liquid (for example a reference standard) in any measurement system, or changes in background current (measured with no glucose input into the sample chamber) in systems that shuttle oxidized and reduced mediator between the electrodes.

The term "counter ion" refers to the portion of an ionic compound that balances the charge of the portion of the compound that performs the function for which it is employed. Thus, in TMA ferri, the ferricyanide ion provides the electron transfer function, and the TMA is a cationic counter ion.

The term "baseline signal" refers to the signal that occurs when a sample containing no analyte is tested with the reagent. In biosensors prepared with reagents containing sodium or potassium ferricyanide, when the baseline signal increases on storage of the dried reagent, it shows that ferrocyanide has been or is being generated (since this is the molecule being detected). The ultimate source of electrons that give the baseline increase need not be established, but it is often associated with the presence of an oxidoreductase enzyme in the reagent.

The term "non-reactive electrode" refers to an electrode that does not by intention participate in the electrochemical reaction for detection of analyte under analytical conditions. Examples of non-reactive electrodes include metal electrodes (gold, platinum, palladium and the like) and carbon electrodes which accept or release electrons without changing the chemical nature of the electrode. This is in contrast to reactive electrodes, such as Ag/AgCl, in which the reaction of silver/silver ions occurs to support the generation of measurable signal.

Dry Reagent Composition

In accordance with a first aspect, the present invention provides a dry reagent composition comprising:

(a) an active redox enzyme that oxidizes/reduces an analyte as a specific substrate to produce an inactive form of the enzyme; and (b) a salt of ferricyanide, wherein the salt of ferricyanide consists of ferricyanide and positively charged counter ions, said positively charged counter ions being selected such that the salt of ferricyanide is soluble in water, has a solubility in water at least twice the maximum analytical concentration of the analyte in the sample but less than the solubility of potassium ferricyanide and/or such that the ferricyanide salt has a lower $E^0{}_{eff}$ at a concentration of 100 mM that is less than that of 100 mM potassium ferricyanide.

As discussed further below, the mechanism by which changing the counterion from potassium can enhance reagent stability and shelf life is not apparent. One possibility initially considered by the inventors is that having a lower $E^0{}_{eff}$ results in less conversion of the ferricyanide to ferrocyanide and therefore decreased baseline increase with storage time. However, when the $E^0{}_{eff}$ of rubidium salts was taken into account, it became apparent that this explanation was inconsistent with the experimental results. Ultimately, the inventors found that there was a correlation between the solubility of the salt in water and the effect observed. In hindsight, this can be explained based on the thermodynamics of crystallization as discussed below. However, it cannot be ruled out that a sufficiently lower $E^0{}_{eff}$ alone or in combination with solubility considerations would not achieve the same effect, and the invention therefore need not be limited to only one mechanistic understanding.

FIG. 1 shows a set of reactions occurring in a test strip containing such a reagent composition, with glucose as the exemplary analyte, glucose oxidase as the exemplary enzyme and TMAferri as the exemplary ferricyanide salt. Glucose reacts with oxidized enzyme glucose oxidase ($GOX_{(ox)}$) to produce gluconic acid and reduced enzyme ($GOX_{(red)}$). $GOX_{(red)}$ reacts with TMA ferri to regenerate $GOX_{(ox)}$ and TMA ferro. This much of the reaction can occur without potential applied at the electrodes 10, 11. When a sufficient potential V is applied to the electrodes 10, 11, electrons can be transferred 12 from electrode 11 to a TMA ferri that is adjacent to electrode 11 to form TMA ferro, while electrons are being transferred 13 from a molecule of TMA ferro that is adjacent to electrode 10 to produce TMA ferri. This electron transfer reaction results in a measurable current. Current also is generated by the same transfer 13 after diffusion 14 of TMAferro from electrode 11 to electrode 12, either of which can be used to provide an indication of glucose concentration. Numerous methods for analyzing these currents are known in the art (for example from U.S. Pat. Nos. 7,501,052, 6,284,125; 5,942,102; 5,352,351; and 5,243,516, and US Publication No. US-2005-0265094-A1, which are incorporated herein by reference), and any type of analysis can be used to analyze the current resulting from the use of this dry reagent composition.

The salt of ferricyanide to be employed may be selected based on the solubility; the salt must be soluble in water and have a lower solubility than potassium ferricyanide, or based on a value of $E^0{}_{eff}$ relative to $E^0{}_{eff}$ of potassium ferricyanide in 100 mM solution. Table 2 lists experimental values for $E^0{}_{eff}$ and solubility for various salts of ferricyanide. As can be seen, $E^0{}_{eff}$ values and the solubilities of sodium ferricyanide and cesium ferricyanide are both greater than for potassium ferricyanide and they therefore do not fall within the scope of the present invention. On the other hand, rubidium ferricyanide and tetramethylammonium ferricyanide have lower solubilities and are within the scope of the invention. In addition, the tetramethylammonium salt has a substantially lower value for $E^0{}_{eff}$.

Other suitable salts of ferricyanide are triammonium ferricyanide and other ammonium or alkylammonium salts. The alkyl groups are selected in size and number so that the salt is water soluble. In general, the alkyl groups of the alkylammonium ions contain from 1 to 3 carbon atoms. The alkyl groups in the alkylammonium ions may be all the same, or may be different. Thus, specific additional examples of alkylammonium ions include tetraethylammonium, trimethylammonium, triethylammonium, dimethyethylammonium, n-propylammonium, The ions in the ferricyanide salt may all be the same. As used in the present application, the term "all the same" refers to a practical rather than an absolute limitation and does not exclude impurity amounts of other counterions that are impractical to remove by cost-acceptable purification techniques. Mixed ion species in which the ions of the ferricyanide are not all the same are also within the scope of the present invention.

The determination of solubility serves to guide the reagent design to a change of the cation in the ferricyanide salt so that thermodynamics favors earlier crystallization of the ferricyanide during reagent drying compared to the usual potassium ferricyanide. Rather than perform extensive formulation experiments, such salts can be readily identified by measuring the solubility of any ferricyanide salt in water and comparing it with that for potassium ferricyanide, or using book values such as those available from Messinger et al. A Dictionary of Chemical Solubilities, Bound 1941, available online from GoogleBooks. Whilst it is possible to do this by a variety of methods, an efficient method is comparing the absorbance spectrum of two saturated solutions, one with potassium ferricyanide and another similar solution that differs only in the substitution of the ion of interest for potassium ions. The absorbance peak at 420 nm is characteristic of the ferricyanide ion and is substantially free from interference from ferrocyanide although corrections for ferrocyanide may be applied using the intensity of absorbance at 320 nm. Alternatively, the ratio of ferricyanide to ferrocyanide in the starting sample can be determined from the Nernst equation if $E^0{}_{eff}$ is known and the electrode potential of solution is measured. Methods of determining an electrode potential are presented in Examples 4 and 5 that remove much of the uncertainty in the starting materials and produce an estimate of $E^0{}_{eff}$ (100 mM), the effective electrode potential according to the Nernst equation determined from experimental data where [ferri]+[ferro]=100 mM, i.e. in concentrated solution.

In a reagent, using a salt of ferricyanide that has a lower solubility and/or a lower $E^0{}_{eff}$ (100 mM) than potassium ferricyanide is a way of achieving improved stability in the baseline. However, this can still be improved upon. The key of the technique is to make sure the ferricyanide crystallizes as the reagent dries and does not leave a residue of some other ferricyanide salt with a higher solubility. Undesired salts can be excluded in either of two ways.

First, if other components of the reagent contain cations that can form undesired salts, alternatives should be sought that contain only the cations of choice in the desired ferricyanide salt. Other ions are frequently found in, for example, buffer salts included to give control of the reagent pH. In the case of an acetate buffer in a rubidium ferricyanide formulation, for example, a buffer stock solution should be formulated using only acetic acid and not acetic acid with sodium or potassium acetate. The pH is then brought to the desired level by titrating the acetic acid with the rubidium hydroxide, thus forming a stock solution of acetate buffer free of sodium or potassium ions that can be used in the formulation. Other preparative methods that exclude undesirable cations will be familiar to those skilled in the art and are within the scope of this invention. By excluding undesirable cations, the only salt of ferricyanide that can crystallize will be the desired salt and so desired, stable phase will be achieved.

Second, in certain cases it is possible to have undesirable cations present, as long as they do not form significant amounts of crystals of the undesirable ferricyanide salt. This can be achieved as a consequence of the solubilities of different phases and some choices of cation may help in this. For example, tetramethylammonium ferricyanide is only soluble at room temperature up to concentrations of about 0.158 M, while potassium ferricyanide is soluble up to 1.11 M at room temperature. The first phase to seed ferricyanide crystal nuclei will therefore be tetramethylammonium ferricyanide and this will then be the preferred crystalline phase under conditions of rapid evaporation. It should be understood, however, that this is a less effective method than exclusion of undesirable ions and may only be generally reliable when the undesirable ions are present in small concentrations.

The dry reagent of the invention may optionally further comprise an electron transfer mediator that is not a salt of ferricyanide. This electron transfer mediator has an electrochemical potential in aqueous medium sufficient to oxidize the inactive reduced form of the enzyme to regenerate active redox enzyme. Numerous compounds suitable for this purpose are known in the art including those described in U.S. Pat. Nos. 5,378,628, 5,393,903, 5,437,999, 5,410,059, 5,589,326, 5,846,702, 6,605,201, 6,676,816, 7,074,308 and 7,090,756, all of which are incorporated herein by reference. In specific embodiments, the electron transfer mediator is an osmium coordination complex such as $Os(dmbpy)_2PicCl$ or $Os(dmbpy)_2Im_2Cl$. These mediators do not have a cationic counter ion. However, if the mediator has a cationic counter ion, then it is desirable to have this counter ion be at least mainly the same as the positively-charged counter ion of the salt of ferricyanide.

Figure 2A:
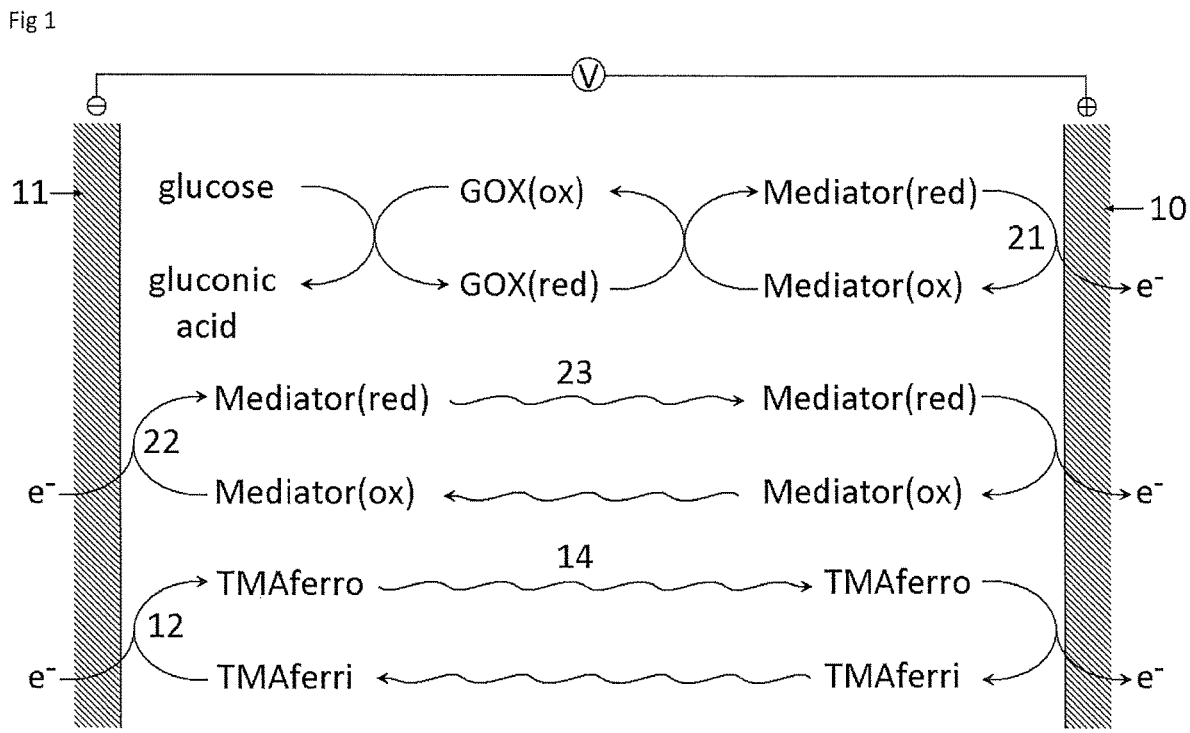
FIGS. 2A, 2B and 2C show alternative sets of reactions that may occur when in a test strip containing a dry reagent in accordance with a second embodiment of the invention when a sufficient potential is applied to the electrodes.
Figure 2B:
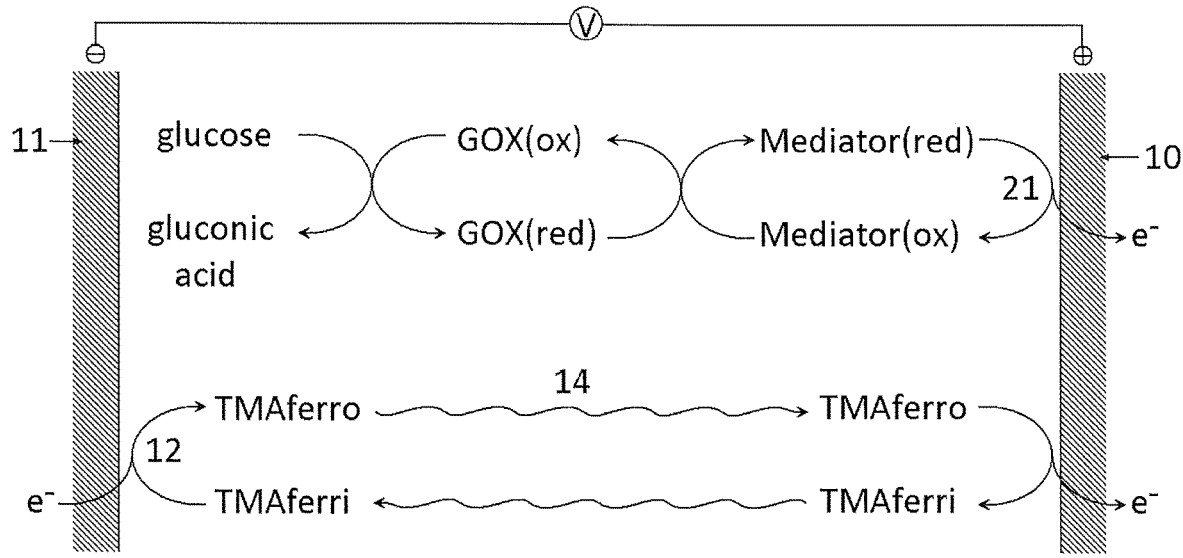
Figure 2C:
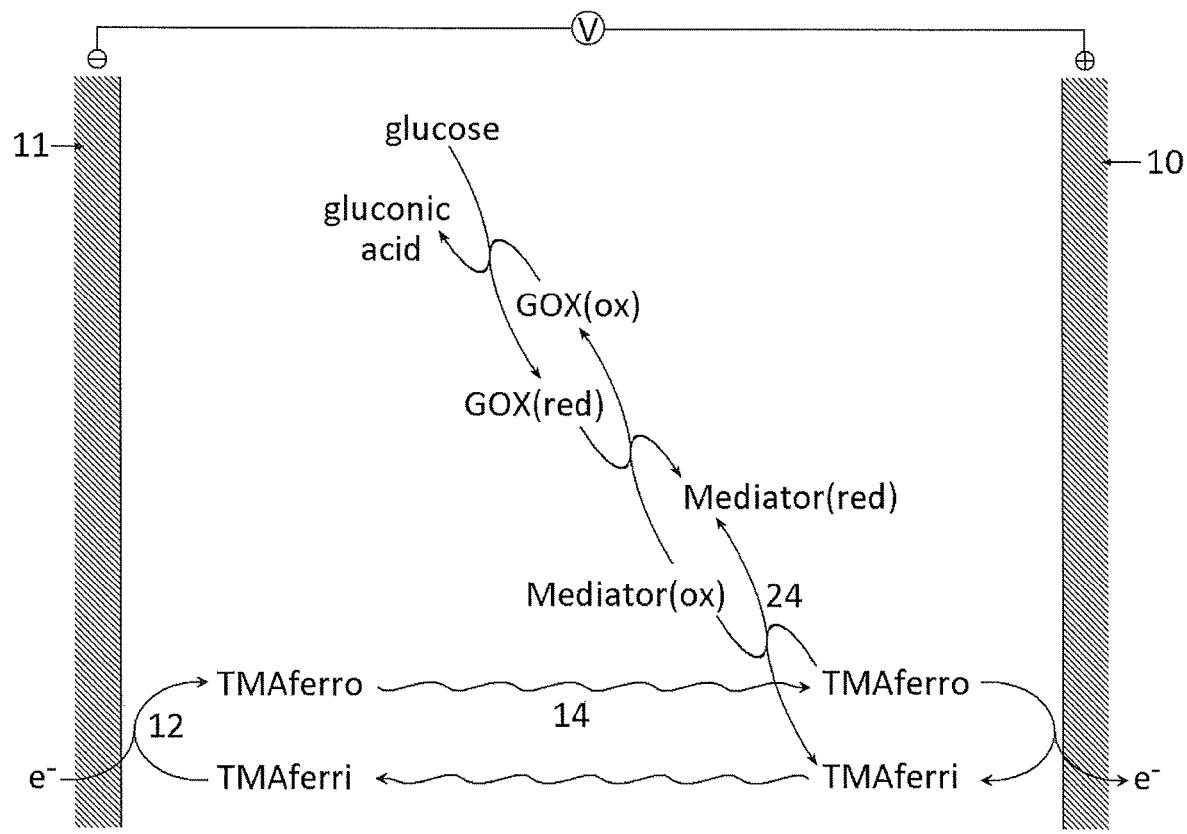

FIGS. 2A-2C show sets of reactions that may occur when a dry reagent containing both TMA ferri and an electron transfer mediator are used to measure glucose. In FIG. 2A, both the mediator couple and the salt of ferricyanide (exemplified as TMA ferri) are capable of being oxidized and reduced at the potential applied between electrodes 10 and 11. Thus, both components function as primary current sources through diffusion processes 14 and 23. In FIG. 2B, the reduction reaction 21 of mediator occurs at electrode 10, but the reverse oxidation of the mediator does not occur at electrode 11. Thus, most of the current 14 due to diffusion between electrodes is generated through the oxidation and reduction of the salt of ferricyanide. In FIG. 2C, the mediator is regenerated by a redox reaction 24 with the salt of ferricyanide. The current is entirely the result of oxidation and reduction of the salt of ferricyanide at the electrodes.

Other electron transfer reactants, such as a catalyst that acts as an electron transfer intermediate between the mediator and the TMA ferri may also be included in the reagent of the invention. (See FIG. 8 of US Patent Publication No. 20070295616). In general, however, it has been observed by the inventors that increasing the number of such materials in the dry reagent has a negative impact on stability of the dry reagent.

The dry reagent of the invention (with or without the electron transfer mediator), may also include an optional buffering agent to optimize activity of the enzymatic reaction. In specific embodiments, this buffering agent is a zwitterion buffering agent comprising a positively-charged buffer counter ion and a buffer conjugate base. Specific examples of suitable conjugate bases are the conjugate base of 3-[N-Tris(hydroxymethyl)methylamino]-2-hydroxypropanesulfonic acid (TAPSO), the conjugate base of piperazine-1,4-bis(2-hydroxypropanesulfonic acid) (POPSO), the conjugate base of 4-(2-hydroxyethyl)-1-piperazineethanesulfonic acid (HEPES) and the conjugate base of N-Tris(hydroxy-methyl)methyl-2-aminoethanesulfonic acid (TES). In specific embodiments, the positively-charged buffer counter ion comprises the same counter ions as the salt of ferricyanide, is mainly the same as the counter ions in the salt of ferricyanide, or has essentially all of the positively-charged buffer counter ion the same counter ion as the salt of ferricyanide.

In particular embodiments of the invention, the dry reagent composition comprises:

(DR1) (a) an active redox enzyme that oxidizes an analyte as a specific substrate to produce an inactive reduced form of the enzyme; and (b) a salt of ferricyanide, wherein the salt of ferricyanide consists of ferricyanide and positively-charged counter ions, said positively charged counter ions being selected such that the salt of ferricyanide is soluble in water, and such that the salt of ferricyanide or the crystalline phase of the salt of ferricyanide has a solubility in water and/or a lower $E^0_{eff}$ at a concentration of 100 mM than potassium ferricyanide.

(DR2) The dry reagent of paragraph (DR1), wherein the salt of ferricyanide includes alkylammonium ions as positively-charged counter ions.

(DR3) The dry reagent of paragraph (DR2), wherein the alkyl groups of the alkylammonium ions contain from 1 to 3 carbon atoms.

(DR4) The dry reagent of paragraph (DR3), wherein the salt of ferricyanide includes tetramethylammonium ions as positively-charged counter ions. In some preferred embodiments, all of the positively-charged counter ions introduced with the salt of ferricyanide are tetramethylammonium ions.

(DR5) The dry reagent of paragraph (DR1), wherein the salt of ferricyanide includes rubidium ions as positively charged counter ions.

(DR6) The dry reagent of any of paragraph (DR1) to (DR5), wherein the positively charged counter ions in the salt of ferricyanide are all the same.

(DR7) The dry reagent of any of paragraphs (DR1) to (DR6), wherein the reagent further comprises an electron transfer mediator that is not a salt of ferricyanide, said electron transfer mediator having an electrochemical potential in aqueous medium sufficient to oxidize the inactive reduced form of the enzyme to regenerate active redox enzyme.

(DR8) The dry reagent of paragraph (DR7), wherein the electron transfer mediator is an osmium coordination complex.

(DR9) The dry reagent of paragraph (DR 8), wherein the osmium coordination complex is $Os(dmbpy)_2PicCl$.

(DR10) The dry reagent of paragraph (DR8), wherein the osmium coordination complex is $Os(dmbpy)_2Im_2Cl$.

(DR11) The dry reagent of any of paragraphs (DR7) to (DR10), further comprising a reduced form of the electron transfer mediator, wherein the amount of said reduced form of the electron transfer mediator relative to the oxidized form of the electron transfer mediator is such that a solution of the reagent has a baseline comparable to the steady-state baseline signal that is produced by a solution of an aged dry reagent in the absence of the reduced form of the electron transfer mediator.

(DR12). The dry reagent of any of paragraphs (DR1) to (DR11), further comprising a salt of ferrocyanide, said salt of ferrocyanide consisting of ferrocyanide and the same positively-charged counter ions as the salt of ferricyanide, wherein the amount of ferrocyanide relative to ferricyanide is such that a solution of dried reagent has a baseline comparable to the steady-state baseline signal that is produced by a solution of an aged dry reagent containing just the ferricyanide and enzyme components of the dried reagent.

(DR13) The dry reagent of any of paragraphs (DR1) to (DR12), further comprising one or more additional compounds in salt form wherein the cations present in the additional compounds are essentially the same as the cations in the salt of ferricyanide.

(DR14) The dry reagent of any of paragraphs (DR1) to (DR13), further comprising a zwitterion buffering agent comprising a positively-charged buffer counter ion and a buffer conjugate base.

(DR15) The dry reagent of paragraph (DR14), wherein the buffer conjugate base is the conjugate base of 3-[N-Tris(hydroxymethyl)methylamino]-2-hydroxypropanesulfonic acid.

(DR16) The dry reagent of paragraph (DR14), wherein the buffer conjugate base is the conjugate base of N-Tris(hydroxy-methyl)methyl-2-aminoethanesulfonic acid.

(DR17) The dry reagent of any of paragraphs (DR14 to (DR16), wherein the positively-charged buffer counter ion comprises the same counter ions as the salt of ferricyanide.

(DR18) The dry reagent of any of paragraphs (DR14) to (DR16), wherein essentially all of the positively-charged buffer counter ion is the same as the counter ion in the salt of ferricyanide.

(DR19) The dry reagent of any of paragraphs (DR1) to (DR18), further comprising a zwitterionic wetting agent comprising a hydrophilic head group including an amine and a sulphonate, and a hydrophobic aliphatic tail of 10 to 16 carbon atoms.

(DR20) The dry reagent of paragraph (DR19), wherein the hydrophobic tail of the zwitterionic wetting agent is a 12 carbon atom tail.

(DR21) The dry reagent of any of paragraphs (DR1) to (DR20), wherein the enzyme is glucose oxidase.

Liquid Composition

The dry reagent as described above can be combined with an aqueous liquid to form a liquid composition in accordance with the invention.

In some embodiments, the aqueous liquid is a sample to be tested for analyte, for example, a body fluid such as blood, interstitial fluid, urine or saliva. The dry reagent is substantially solvated and dispersed in the aqueous liquid so that electron transfer reactions as described in FIGS. 1, and 2A-2c can occur.

When the liquid composition is formed or introduced into the sample cell of a test strip for measurement of analyte, the concentration of enzyme in the aqueous liquid is preferably 18 mg/ml or greater and more preferably 27 mg/ml or greater.

When the reagent contains $Os(dmbpy)_2PicCl$ and the liquid composition is formed or introduced into the sample cell of a test strip for measurement of analyte, the $Os(dmbpy)_2PicCl$ is suitably present at a concentration of from 0.5 to 2.0 mg/ml and more preferably 0.8 to 1.0 mg/ml.

When a buffering agent is present in the reagent, the buffering agent suitably has a concentration in the liquid composition sufficient to provide a buffer capacity to pH 6.8 in excess of 22 mM. When the buffering agent comprises the conjugate base of 3-[N-Tris(hydroxymethyl)methylamino]-2-hydroxypropanesulfonic acid (TAPSO), the concentration of buffering agent is suitably 50 to 200 mM. Suitably, the buffering agent maintains the pH of the liquid composition in the range of pH 7 to 8 which is compatible with most enzymes.

A liquid composition in accordance with the invention may also be used during manufacture of test strips. The liquid composition containing the reagent is placed onto an electrode or into the sample chamber and allowed to dry. The concentration of the reagent in the liquid composition is sufficient to deliver an amount of reagent that will achieve operative levels of the enzyme, the salt of ferricyanide and the electron transfer mediator (if present) when a sample volume is added to the test strip.

Thus, in some embodiments, the liquid of the composition of the invention comprises:

(LC1). the reagent of any of paragraphs (DR1) to (DR 21) and an aqueous liquid carrier, for example blood, interstitial fluid, urine or saliva.

(LC2). The liquid composition of paragraph (LC1), wherein the concentration of enzyme in the aqueous liquid carrier is 27 mg/ml or greater.

(LC3). The liquid composition of paragraph (LC1) or (LC2), wherein the reagent contains $Os(dmbpy)_2PicCl$ at a concentration of from 0.8 to 1.0 mg/ml.

(LC4) The liquid composition of any of paragraphs (LC1) to (LC3), wherein buffering agent is present in the reagent and has a concentration in the liquid composition sufficient to provide a buffer capacity at pH 6.8 in excess of 22 mM.

(LC5) The liquid composition of paragraph (LC4), wherein the buffering agent comprises the conjugate case of 3[N-Tris(hydroxymethyl)methylamino]-2-hydroxypropane-sulfonic acid, and the concentration of buffering agent is 50 to 200 mM.

(LC6) The liquid composition of any of paragraphs (LC1) to (LC5), wherein the buffering agent maintains the pH of the composition in the range of pH 7 to 8, preferably 7.6 to 7.8.

Test Strip

The invention also provides a test strip that incorporates the dry reagent as discussed above. As pictured in FIG. 3, the test strip comprises (a) first electrode 31 in one part of the strip construction 32 and second electrode 33 in a second part of the strip construction;

(b) a sample cell 35 for receiving a liquid sample formed by assembling the strip 38, wherein a liquid sample disposed within the sample cell 35 is in contact with the first and second electrodes 31, 33; and (c) a dry reagent deposited on exposed electrode 31 before assembly and (d) exposed surfaces 36 that allow electrical contact to be made to the electrodes 31 and 33.

The dry reagent is disposed such that upon application of a liquid sample to the test strip the dry reagent dissolves in the sample within the sample cell. For example, as shown and is conventional in commercially available test strips, the dry reagent may be disposed within the sample cell prior to application of a liquid sample.

The first and second electrodes are suitably made from an inert material with suitable conduction e.g. carbon or a metal such as gold, palladium or platinum. In some embodiments with carbon electrodes, the carbon is prepared in the form of a screen-printable ink. In some embodiments, at least one of the first and second electrodes comprises palladium. In some embodiments, both of the first and second electrodes comprise palladium. In other embodiments, at least one of the first and second electrodes, or both of the first and second electrodes comprise gold. The electrodes may be of equal or different size, and may be made from the same or different materials.

Figure 3:
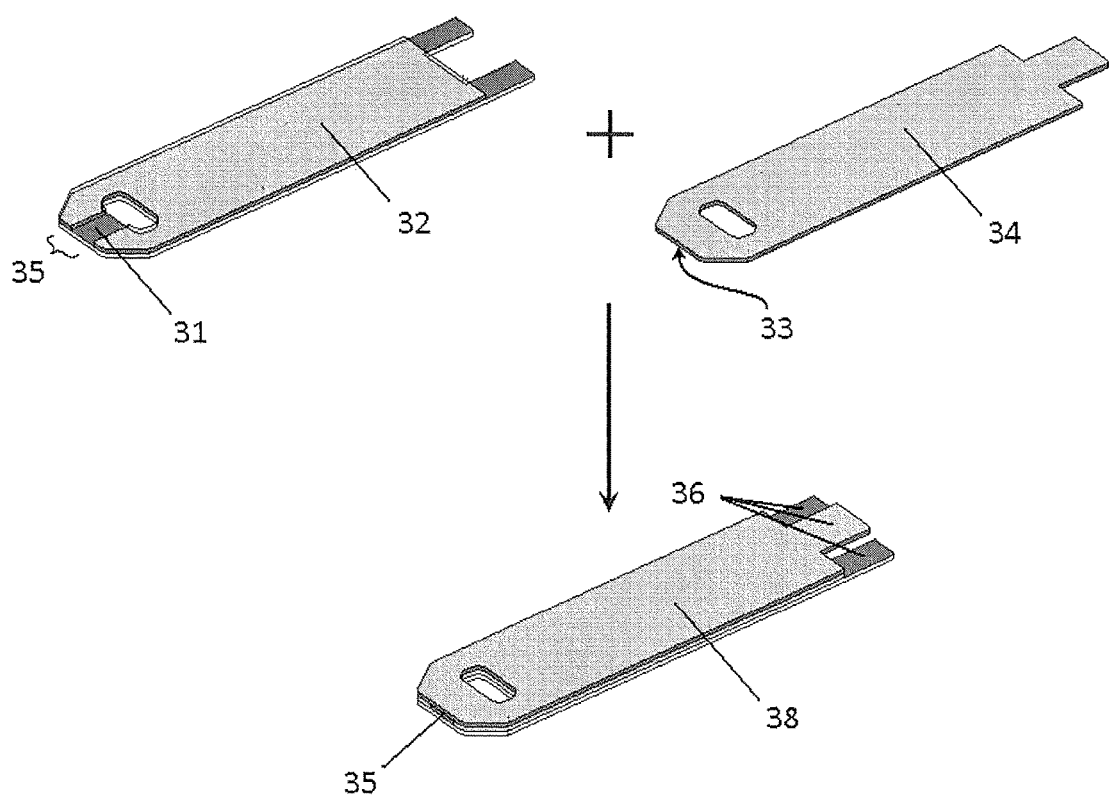
FIG. 3 shows a test strip in accordance with the invention.

The electrodes may be in a facing configuration as shown in FIG. 3, but may also be in a coplanar configuration. When in the facing configuration, the dry reagent may be suitably disposed as described in US-2005-0258036 A1, which is incorporated herein by reference, on one electrode and extending upwards along the walls of the cells in a U-shaped configuration.

To minimize the amount of sample required for performing the test, the sample cell is preferably quite small, for example having a volume of less than 1 preferably less than 500 nl, more preferably less than 300 nl. Such sample volumes are known and used in conventional commercially available test strips, consistent with the well understood goal of reducing sample volume to the extent possible to minimize pain to a person undergoing testing.

In some embodiments of the invention, the test strip comprises (TS1) (a) first and second non-reactive electrodes;

(b) a sample cell for receiving a liquid sample, wherein a liquid sample disposed within the sample cell is in contact with the first and second electrodes; and (c) a dry reagent, wherein said dry reagent is disposed such that upon application of a liquid sample to the test strip the dry reagent dissolves in the sample within the sample cell.

(TS2) The test strip of paragraph (TS1), wherein the dry reagent is disposed within the sample cell prior to application of a liquid sample.

(TS3). The test strip of paragraph (TS1) or (TS2), wherein the first and second electrodes are metal electrodes.

(TS4). The test strip of any of paragraphs (TS1) to (TS3), wherein at least one of the first and second electrodes comprises palladium.

(TS5). The test strip of paragraph (TS4), wherein both of the first and second electrodes comprise palladium.

(TS6). The test strip of any of paragraphs (TS1) to (TS3), wherein at least one of the first and second electrodes comprises gold.

(TS7). The test strip of paragraph (TS6), wherein both of the first and second electrodes comprise gold.

Method for Testing for Analyte

A further aspect of the present invention is a method for testing for an analyte in a liquid sample. The method comprises the steps of:

(a) applying a liquid sample to a test strip incorporating a dry reagent as described above; wherein the enzyme in the dried reagent is selected to be specific for the analyte;

(b) applying an external signal to the test strip to generate a signal indicative of the amount of analyte in the sample.

In specific embodiments of the invention, the liquid sample is blood. In specific embodiments of the invention, the analyte is glucose and the enzyme is glucose oxidase.

In specific embodiments of the invention, the external signal is a potential applied between the first and second electrodes of the test strip, and a current is measured as the signal indicative of the amount of analyte in the sample. Methods for making measurements of this type are known in the art, for example from the patents and publications noted above, and may be referred to as amperometric measurements. Coulometry is related to amperometry in that the total charge passed in a period of time (integral of the current signal) is measured.

In other embodiments of the invention, the applied signal is a current, and what is measured is a potential. (See U.S. Pat. No. 5,413,690 and US Publication 2010/0025265, which are incorporated herein by reference).

In some embodiments the method of the invention is:

(MT1) A method for testing for an analyte in a liquid sample comprising the steps of:

(a) applying a liquid sample to a test strip in accordance with any of paragraphs (TS1) to (TS7); wherein the enzyme in the dried reagent is selected to be specific for the analyte; and (b) applying an external signal to the test strip to generate a signal indicative of the amount of analyte in the sample.

(MT2). The method of paragraph (MT1), wherein the external signal is a potential that is applied between the first and second electrodes of the test strip, and a current is measured as the signal indicative of the amount of analyte in the sample.

(MT3) The method of paragraph (MT1) or (MT2), wherein the liquid sample is blood.

(MT4) The method of any of paragraphs (M1) to (M3), wherein the analyte is glucose and the enzyme is glucose oxidase.

Method for Forming a Shelf Stable Reagent

In a further aspect, the invention provides a method for forming a shelf-stable reagent for use in testing for an analyte such as glucose. This is of particular relevance when the reagent is stored in test strips with gold electrodes because of the potential for gold electrodes to interact with the reagent.

In specific embodiments, this aspect of the invention includes:

(SS1) A method for forming a shelf stable electrochemical test reagent for use in detection of an analyte comprising the steps of:

(a) selecting an oxidoreductase enzyme that oxidizes/reduces the analyte as a specific substrate;

(b) selecting a salt of ferricyanide, wherein the salt of ferricyanide consists of ferricyanide and selected positively-charged counter ions, said positively-charged counter ions being selected such that the salt of ferricyanide is soluble in water, and such that the salt of ferricyanide or the crystalline phase of the salt of ferricyanide has a solubility in water and/or a lower $E^0_{eff}$ at a concentration of 100 mM than potassium ferricyanide; and (c) combining the selected enzyme and the selected salt of ferricyanide to form a shelf stable electrochemical test reagent for use in detection of the analyte.

(SS2) The method of paragraph (SS1), wherein the selected salt of ferricyanide includes alkylammonium ions as positively-charged counter ions.

(SS3) The method of paragraph (SS2), wherein the alkyl groups of the alkylammonium ions contain from 1 to 3 carbon atoms.

(SS4). The method of paragraph (SS3), wherein the salt of ferricyanide includes tetramethylammonium ions as positively-charged counter ions.

(SS5). The method of paragraph (SS3), wherein the salt of ferricyanide includes rubidium ions as positively charged counter ions.

(SS6). The method of any of paragraphs (SS1) to (SS5), wherein the positively-charged counter ions in the selected salt of ferricyanide are all the same.

(SS7). The method of any of paragraphs (SS1) to (SS6), wherein the reagent further comprising the step of selecting an electron transfer mediator that is not a salt of ferricyanide, said electron transfer mediator having an electrochemical potential in aqueous medium sufficient to reduce/oxidize the inactive reduced form of the enzyme to regenerate active redox enzyme, and including the selected electron transfer mediator in the reagent.

(SS8). The method of paragraph (SS7), further comprising the step of including in the reagent a reduced form of the electron transfer mediator, wherein the amount of said reduced form of the electron transfer mediator relative to the oxidized form of the electron transfer mediator is such that a solution of the reagent has a baseline comparable to the steady-state baseline signal that is produced by a solution of an aged dry reagent in the absence of the reduced form of the electron transfer mediator.

(SS9). The method of paragraph (SS7) or (SS8), wherein the electron transfer mediator is an osmium coordination complex.

(SS10) The method of paragraph (SS9), wherein the osmium coordination complex is $Os(dmbpy)_2PicCl$.

(SS11) The method of paragraph (SS9), wherein the osmium coordination complex is $Os(dmbpy)_2Im_2Cl$.

(SS12) The method of any of paragraphs (SS1) to (SS11), further comprising the step of including in the dry reagent a salt of ferrocyanide, said salt of ferrocyanide consisting of ferrocyanide and the same positively-charged counter ions as the salt of ferricyanide, wherein the amount of ferrocyanide relative to ferricyanide is such that a solution of dried reagent has a baseline comparable to the steady-state baseline signal that is produced by a solution of an aged dry reagent containing just the ferricyanide and enzyme components of the dried reagent.

(SS13) The method of any of paragraphs (SS1) to (SS12), further comprising the step of adding a zwitterion buffering agent comprising a positively-charged buffer counter ion and a buffer conjugate base to the reagent.

(SS14) The method of paragraph (SS13), wherein the buffer conjugate base is the conjugate base of 3[N-Tris(hydroxymethyl)methylamino]-2-hydroxypropanesulfonic acid.

(SS15). The method of paragraph (SS13), wherein the conjugate base is the conjugate base of N-Tris(hydroxymethyl)methyl-2-aminoethanesulfonic acid.

(SS16) The method of any of paragraphs (SS13) to (SS15), wherein the positively-charged buffer counter ion comprises the same counter ions as the selected salt of ferricyanide.

(SS17) The method of any of any of paragraphs (SS13) to (SS15), wherein the positively-charged buffer counter ion consists essentially of the same counter ion as the selected salt of ferricyanide.

(SS18) The method of any of paragraphs (SS1) to (SS17), further comprising the step of adding a zwitterionic wetting agent comprising a hydrophilic head group including an amine and a sulphonate, and a hydrophobic aliphatic tail of 10 to 16 carbon atoms to the reagent.

(SS19). The method of paragraphs (SS18), wherein the hydrophobic tail of the zwitterionic wetting agent is a 12 carbon atom tail.

(SS20) The method of any of paragraphs (SS1) to (SS19), wherein the enzyme is glucose oxidase.

Buffer Composition of the Invention

In a further aspect of the invention, a buffer solution is provided comprising a buffering agent formed from 3-[N-Tris(hydroxymethyl)methylamino]-2-hydroxypropanesulfonic Acid, and the tetramethylammonium salt of the conjugate base of 3-[N-Tris(hydroxymethyl)methylamino]-2-hydroxypropanesulfonic Acid.

Benefits of the Invention

Ferricyanide (generally potassium ferricyanide) is a well-understood and relatively inexpensive electron transfer mediator which continues to be used in various commercial test strips, in particular for measurement of glucose. However, as noted above, potassium ferricyanide has problems. The present invention overcomes these problems, and thus facilitates the continued use of ferricyanide in this capacity.

Figure 4:
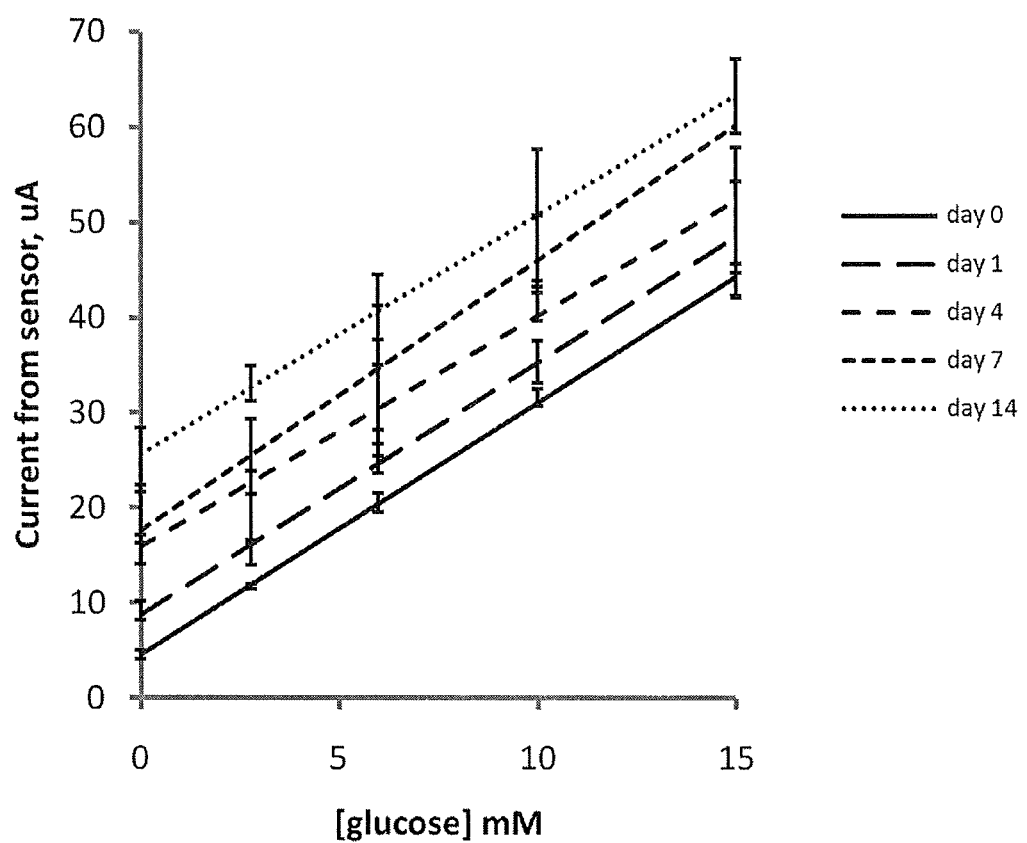
FIG. 4 shows measured current as a function of glucose concentration for a test strip made using a dry reagent containing glucose oxidase, potassium ferricyanide and Os(dmbpy)₂PicCl. The aging conditions were that strips were held in desiccator vials at 50° C.; aging times are as noted in the figure.
Figure 5:
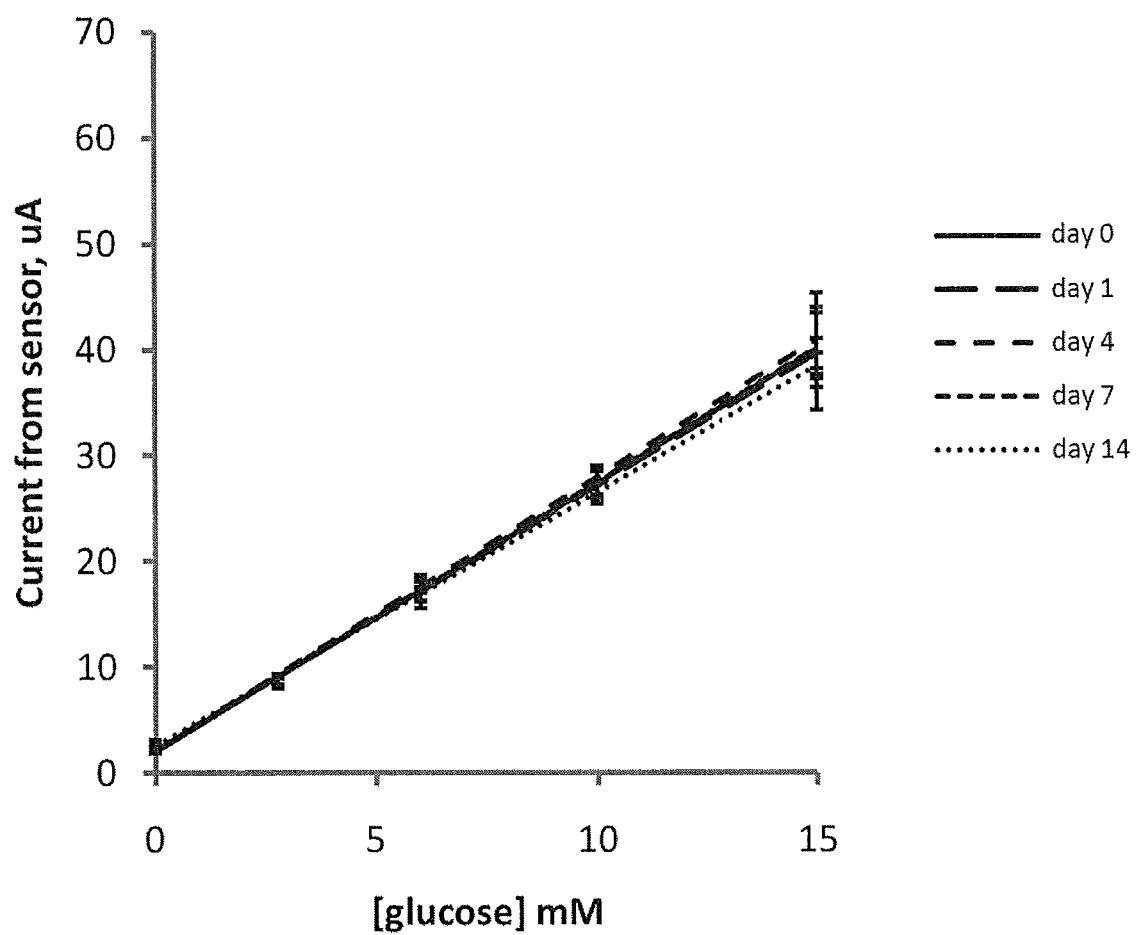
FIG. 5 shows measured current as a function of glucose concentration for a test strip made using a dry reagent containing glucose oxidase, TMA ferri and Os(dmbpy)₂PicCl. Aging is as for FIG. 4.

FIG. 4 shows measured current as a function of glucose concentration for a test strip made using a dry reagent containing glucose oxidase, potassium ferricyanide and $Os(dmbpy)_2PicCl$ (See example 11) after various periods of accelerated again. As can be seen, the measured current at any given concentration substantially increases with aging time. FIG. 5 shows the results of the same experiment in test strips that contain TMA ferri in place of potassium ferricyanide. There are no changes in the amount of current measured regardless of the aging time.

Figure 6:
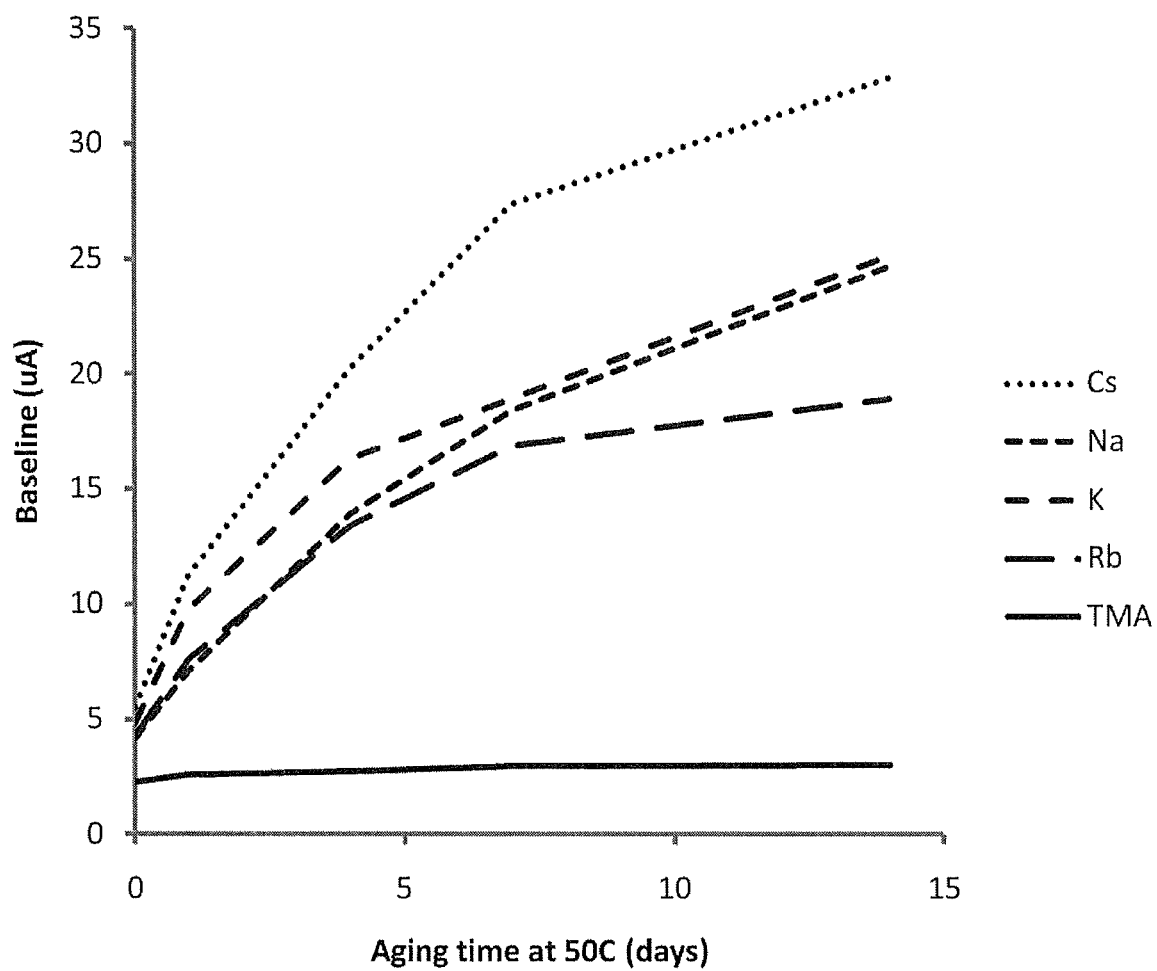
FIG. 6 shows changes in baseline current (no glucose in test liquid) for different salts of ferricyanide as a function of aging time. Aging is as for FIG. 4.
Figure 7:
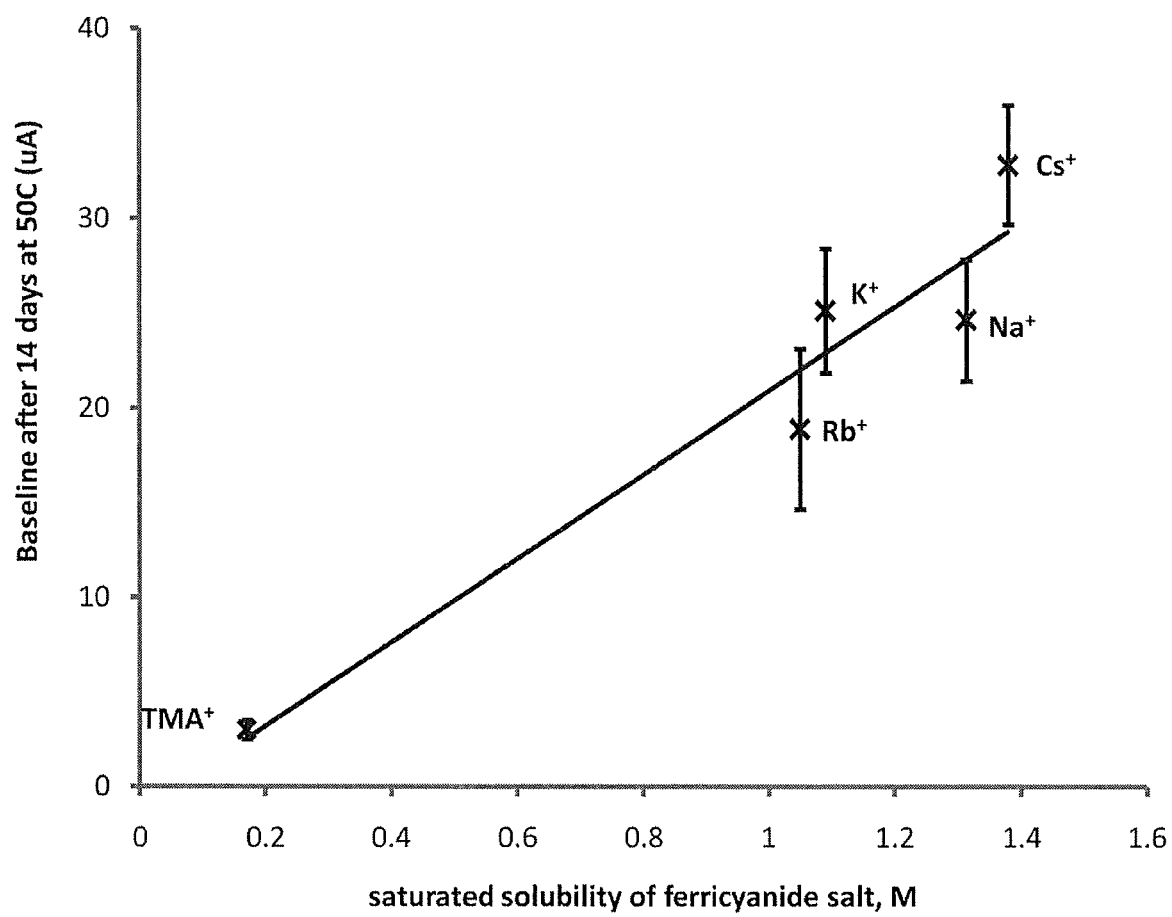
FIG. 7 shows the correlation between the baseline current from strips held at 50° C. in desiccator vials with the saturated solubility of the ferricyanide salt in the reagent in those strips

Without intending to be bound by any specific mechanism, it is believed that this change in current results from conversion of part of the ferricyanide to ferrocyanide during the aging process. This results in a baseline current between the electrodes that occurs even in the absence of glucose in the sample. FIG. 6 shows the relationship of this baseline current for various salts. TMA ferri is clearly the best of the salts tested. However, rubidium ferricyanide is also superior because the increase in baseline current tends to level out to a lower level than the potassium salt, making it easier to compensate for changes due to aging. The correlation between the baseline after 14 days of aging at 50° C. and the saturated solubility of the salt is shown in FIG. 7. Again, without intending to bound to any specific mechanism, it is believed these results show that a glassy phase forms in the reagent as the final parts of the wet reagent dry out; the amount of ferricyanide trapped in this glassy phase is dependent on the solubility of the ferricyanide salt and a set portion of this ferricyanide converts to ferrocyanide to give the baseline signal, until a limiting ratio of ferri:ferro is reached.

Figure 8:
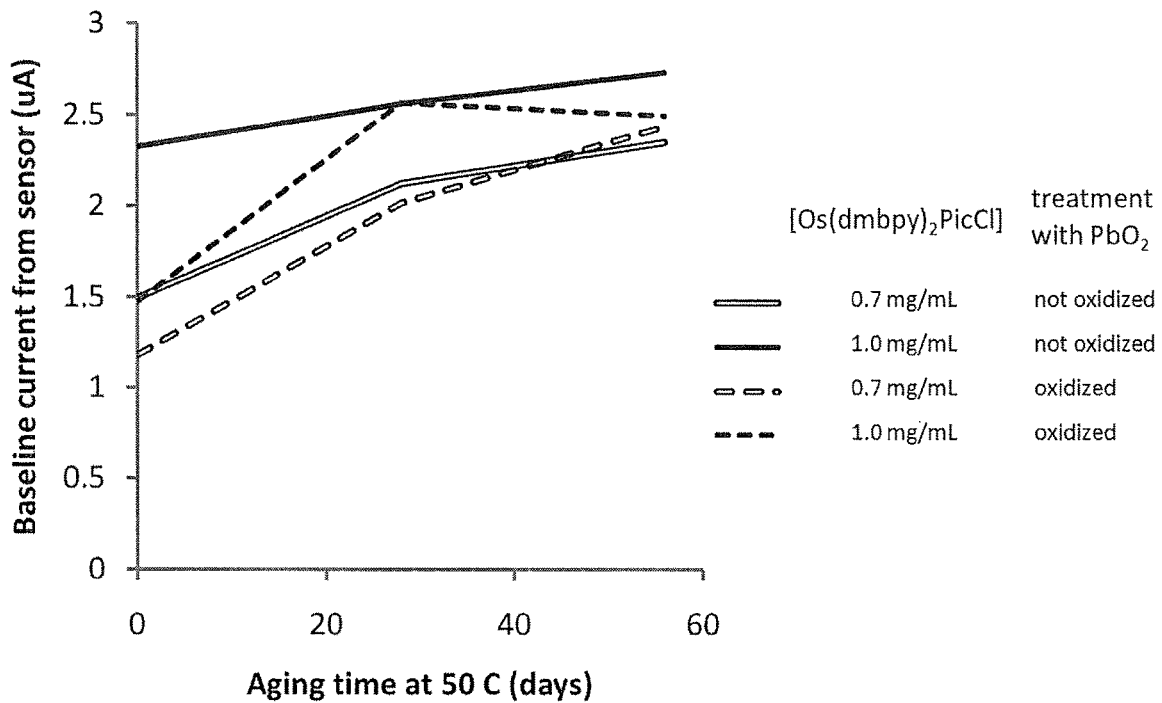
FIG. 8 shows the evolution of the baseline current with aging time for strips held at 50° C. in desiccator vials. The reagents are as described in Example 15.

A baseline signal that changes over the course of the strip shelf life is a large source of error in strip performance. This error can be managed by either specifying poorer performance tolerances for a strip or a shorter shelf life of the product There is therefore a benefit not only in having a low limit for the highest baseline but also from having only a small change in the baseline over the course of the strip shelf life. From aging experiments like those of FIGS. 4, 5 and 6 it is possible to establish the limit of the baseline rise, which usually stabilizes by 14 days at 50° C. It is therefore an advantage to introduce ferrocyanide into the wet reagent before making strips so that the baseline of freshly made strips will already be at this level at the start of the strip life. Alternatively, a different reducing agent can be added to the solution to generate ferrocyanide in situ. It is an advantage if this reducing agent is another of the already identified components of the reagent, since this prevents introducing impurities. It is a particular advantage if that component is an electron transfer mediator for the enzyme, for example $Os(dmbpy)_2PicCl$, since the reduced form of this type of compound is preparatively much easier to handle (the reduced forms of such complexes often have lower solubility so are more easily isolated and, because of their electronic configuration, their purity can be established by the standard analytical technique of n.m.r., whereas the oxidized forms cannot). The stability of the baseline can be examined by comparing strips where the reduced mediator has been used in a reagent compared to strips where the same reagent has been oxidized first with $PbO_2$ to force the baseline current lower. This is described in Example 15 and the effect is illustrated in FIG. 8, which shows that the presence of a reduced component in the reagent gives a more stable baseline current from the sensor.

In addition, the reagent of the present invention experiences less loss of enzyme activity as test strips age. This allows the use of less enzyme in each test strip while being able to maintain high levels of performance.

Example 1 Synthesis of Tetramethylammonium Ferricyanide

Dowex 50WX2-200(H) ion exchange resin was added to DI water and shaken to form a slurry. This slurry was poured into a glass column with a glass porous frit and PTFE stopcock. The column was also wrapped with UV filtering plastic. More slurry was added and the liquid run out until the depth of resin settled out to give a column volume of 58 ml. The column was rinsed with DI water: initially the eluent was orange but rinsing was continued until the eluent ran clear. 20 ml of 1M HCl was added and run through the column: this caused the column volume to shrink to 45 ml. The acid was rinsed out of the column until the pH of the eluent was ~pH6 (measured on pH paper) by which time the column volume had also restored to 58 ml by swelling of the resin. 25 collection pots were assembled, each with volume >10 ml and each was charged with 400 ul of a 25 wt % solution of tetramethylammonium hydroxide in water. 8 ml of 1M potassium ferricyanide was added to the column; by the time all 8 ml had run into the column the eluent out the bottom was showing a yellow tinge and was pH~4. Collection of the eluent was started in the first collection pot and an immediate precipitate formed but this dissolved as the contents of the pot became acidic. The eluent collection was switched to the next pot every time the contents became acidic and for all of the first eight pots precipitate was observed that dissolved when the contents became acidic. The ninth to 15$^{th}$ pots became acidic without complete dissolution of the precipitate, and the supernatant was green and very concentrated. This colour was a paler yellow for the sixteenth pot and by the seventeenth pot no precipitate formed, and the eluent became paler and paler. Collection was stopped at this point and the acidified contents of all pots were combined; they were then neutralized with more of the 25 wt % solution of tetramethylammonium hydroxide in water and the total volume of the hydroxide required for neutralization was calculated as 8.6 ml (including the contents of 17 collection pots). This is equivalent to 2.15 g of tetramethylammonium hydroxide i.e. 23.58 mmoles, which compares well with the 24 mmoles of potassium ions exchanged from the original potassium ferricyanide solution. The neutralized, yellow solution of tetramethylammonium ferricyanide was cooled in an ice bath and the crystals grew as flakes which were isolated by suction filtration and dried in a vacuum desiccator, yield 2.517 g, 67% based on the dihydrate. Higher yields can be obtained by cooling in a salt-ice bath (>80% after 2 hours)

Example 2 Synthesis of Rubidium Ferricyanide

The ion-exchange column was prepared as in Example 1 and 20 collection pots with volume between 3-10 ml were prepared, each being charged with 200 ul of a 50 wt % solution of rubidium hydroxide in water. 10 ml of potassium ferricyanide were added and run into the column. The collection of the eluent was performed under fluorescent lights that were fitted with UV-absorbent covers. The eluent collection was started with the first pot and switched to the next pot every time the contents became acidic, monitored by pH paper. The pot solutions were clear and yellow, except when the contents become extremely acidic, in which case they become green. This yellow colour was a paler yellow for the eighteenth pot and by the nineteenth pot the eluent had became paler and paler. Collection was stopped at this point and the acidified contents of all pots were combined; they were then neutralized with more of the 50 wt % solution of rubidium hydroxide in water and the total volume of the hydroxide required for neutralization was calculated as 3.4 ml (including the contents of 17 collection pots). This is equivalent to 28.87 mmoles of rubidium hydroxide, which compares well with the 30 mmoles of potassium ions exchanged from the original potassium ferricyanide solution. The neutralized, yellow solution of rubidium ferricyanide was concentrated by heating gently on a hot plate until the nearly boiling solution showed the first evidence of crystals forming (at about 12 ml) and cooling the concentrated solution allowed orange ferricyanide crystals to slowly form. The crystals were isolated by suction filtration and dried in a vacuum dessicator. The yield of rubidium ferricyanide is approximately 3.66 g, 78% based on MWt of rubidium ferricyanide at 468.39 g/mol.

Example 3 Synthesis of Rubidium Ferrocyanide

The filtrate from Example 2 was mixed with ethanol to generate a 50:50 aqueous ethanol solution, which generated an immediate precipitate of a pale yellow color. Heating this solution to boiling and then slowly allowing the alcohol to distil off gave a clear solution that was allowed to cool slowly overnight to give pale yellow crystals. The crystals were isolated by suction filtration and dried in a vacuum desiccator, to give 1.05 g of rubidium ferrocyanide trihydrate, 1.72 mmoles based on a rmm of 607.87 g/mol and a further 17.2% of the initial ferricyanide recovered.

Example 4 Measuring the Effective Electrode Potential of Potassium Ferricyanide Stock solutions of potassium ferricyanide (0.3293 g in 10 ml, 100 mM, labeled 'A') and potassium ferrocyanide (0.4224 g of the trihydrate in 10 ml, 100 mM, labeled 'B') were prepared. 4 ml of stock solution A was measured out and the chemical potential of the solution was measured using an ORP electrode. Further ORP measurements were taken after adding the following aliquots of stock solution B: 40 ul, 46 ul (i.e. 86 ul total), 100 ul (186 ul total), 214 ul (400 ul total), 460 ul (860 ul total), 1000 ul, (1860 ul total), 2140 ul (4000 ul total). Similarly, 4 ml of stock solution B was measured out and the chemical potential of the solution was measured using an ORP electrode. Further ORP measurements were taken after adding the following aliquots of stock solution A: 40 ul, 46 ul (i.e. 86 ul total), 100 ul (186 ul total), 214 ul (400 ul total), 460 ul (860 ul total), 1000 ul, (1860 ul total), 2140 ul (4000 ul total). The data of total volumes of A and B in each solution and the ORP reading of each were entered in a spread sheet for fitting to the Nernst equation. The concentrations of the stock solutions were not assumed to be pure: stock solution A was assumed to have an unknown concentration 'a' mM of ferricyanide and hence a concentration 100-a mM of ferrocyanide and an initial value of a=99.9 mM was set in the spreadsheet.

Figure 9:
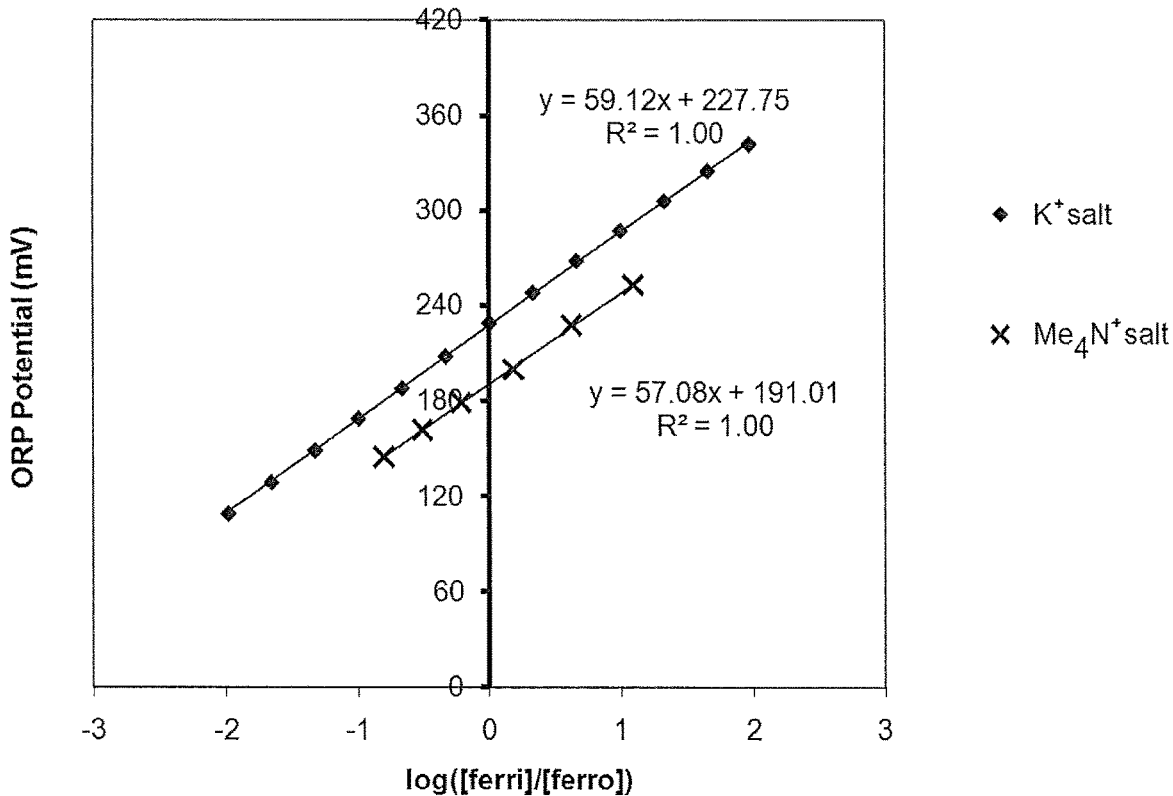
FIG. 9 shows a plot of chemical potential as measured by an ORP electrode against the log of the concentration ratio of ferri vs ferro.

Similarly, stock solution B was assumed to have an unknown concentration 'b' mM of ferrocyanide and hence a concentration 100-b mM of ferricyanide with an initial value of b=99.9 mM being set in the spreadsheet. Concentrations of ferricyanide and ferrocyanide were then calculated for each mixture and a graph of ORP reading vs log([ferri]/[ferro]) was plotted. The values of 'a' and 'b' were varied until the graph became linear and the slope of the mixtures was close to 59.4 mV per decade of change in the concentration ratio. The intercept of the ORP axis with log([ferri]/[ferro])=0 was determined and this was the measure of $E^O$ (100 mM), the standard electrode potential according to the Nernst equation but measured at [ferri]+[ferro]=100 mM. The results are shown in FIG. 9

Example 5 Measuring the Effective Electrode Potential of Tetramethylammonium Ferricyanide Stock solutions of tetramethylammonium ferricyanide (0.470 g of the dihydrate in 10 ml, 100 mM, labeled 'A') and tetramethylammonium ferrocyanide (0.4964 g in 5 ml, 100 mM, labeled 'B') were prepared. The chemical potentials of the stock solutions were measured. ORP readings of the following mixtures of the stock solutions were also measured: {0.3 ml A+2.7 ml B}, {0.15 ml A+2.85 ml B}, {0.3 ml A+2.7 ml B}, {0.75 ml A+2.25 ml B}, {1.5 ml A+1.5 ml B}, {2.25 ml A+0.75 ml B}, {0.3 ml A+2.7 ml B}. The data of total volumes of A and B in each solution and the ORP reading of each were entered in a spread sheet for fitting to the Nernst equation as described in Example 4 and the results are shown in FIG. 9

Example 6 Calibrating the Absorbance of Potassium Ferricyanide

Figure 10:
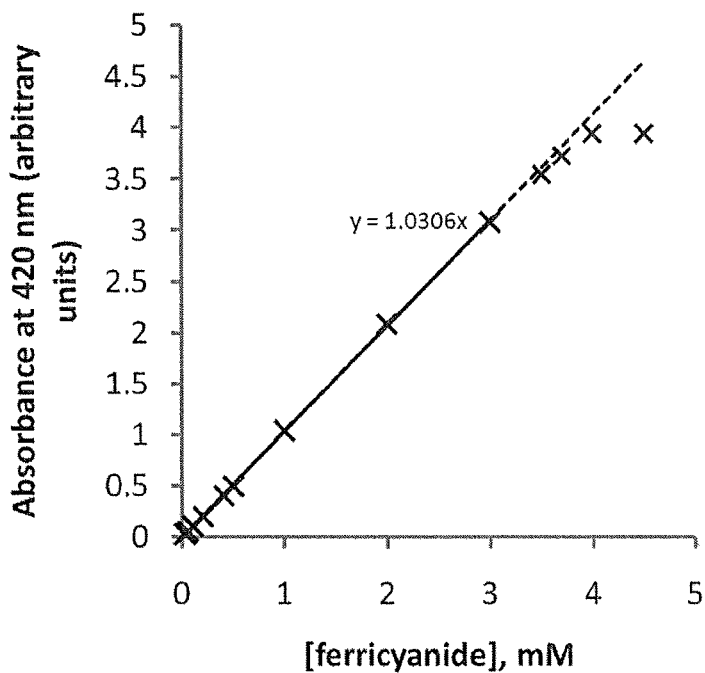
FIG. 10 shows the absorbance intensity at 420 nm of potassium ferricyanide as a function of ferricyanide concentration

A stock solution of 1 M potassium ferricyanide was prepared by dissolving 1.6463 g of potassium ferricyanide in water, made up to a volume of 5 mL in a volumetric flask. 1 mL of this solution was placed in a 100 mL volumetric flask and diluted to 10 mM by making the volume up to 100 mL with water. Dilutions of this 10 mM solution were prepared in cuvettes to cover the concentration range from 0.025 to 4.5 mM and the UV/Vis spectrum of the dilution recorded as soon as the solution was prepared. The absorbance of a water sample was subtracted to correct for the baseline absorbance. The absorbance intensity of the peak at 420 nm was measured from the baseline-subtracted spectrum and plotted against concentration of the cuvette solution. The graph was inspected to determine the linear range of the absorbance and an absorbance per mole of ferricyanide determined from data within this linear range as shown in FIG. 10.

Figure 11:
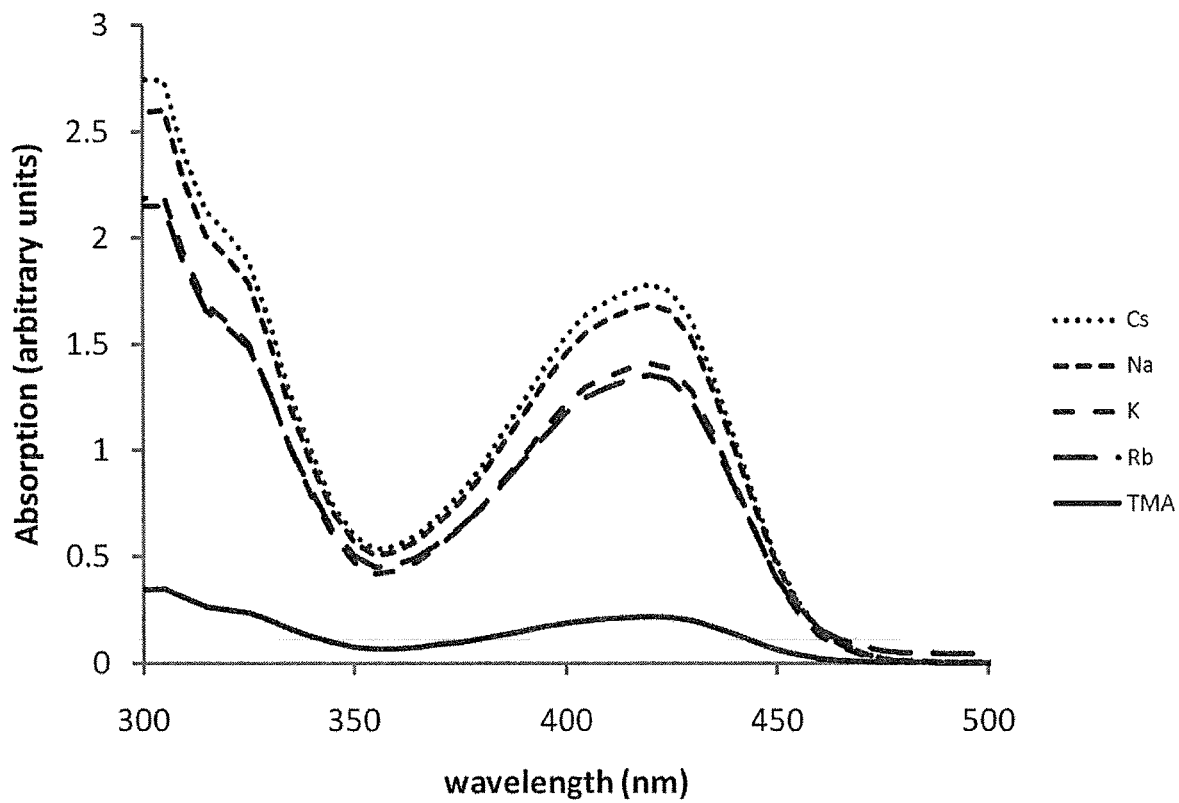
FIG. 11 shows example UV/Vis spectra for a variety of saturated ferricyanide solutions all diluted 800:1.

Example 7 Measuring the Saturated Concentration of Tetramethylammonium Ferricyanide A sample of tetramethylammonium ferricyanide crystals was placed on a sheet of aluminium foil and the foil folded over to cover the sample. This was placed carefully in a mortar and the crystals crushed by tapping with a pestle. The foil and crushed crystals were lifted out of the pestle and the crushed crystals poured into an eppendorf tube. A small amount of water was added and the solution was shaken to dissolve as much solid as possible, then left for at least an hour to equilibrate. The sample was inspected to assure that some solid still remained and then 10 uL of the solution was extracted with a pipette and mixed into 990 uL of water in a cuvette. The cuvette was placed in a UV/Vis spectrometer and the absorbance spectrum recorded between 200 and 600 nm. The absorbance at 420 nm was used in combination with the calibration of Example 6 to determine the saturated concentration: the TMAferri absorbance was 1.5317 at 420 nm and the calibration slope was [ferricyanide]=1.03×absorbance, giving [ferricyanide]=1.58 mM for the 100:1 dilution and 0.158 M for the saturated concentration of TMA ferri. Example spectra for a variety of saturated solutions measured by this method are shown in FIG. 11.

Example 8 Synthesis of TMA Salt of TAPSO Buffer, pH 7.5

5.18 g of 3[N-Tris(hydroxymethyl)methylamino]-2-hydroxypropanesulfonic Acid (TAPSO) were weighed in a 100 ml beaker and 30 ml of water was added to dissolve the solid. Sufficient 25 wt % tetramethylammonium hydroxide was added to bring the pH to 7.5 and the contents of the beaker were then poured into a 50 ml volumetric flask. The beaker was rinsed to make sure all the TAPSO was transferred into the volumetric flask and the volume of solution was brought up to 50 ml with more water.

TMA-TAPSO buffers represent a further aspect of the present invention.

Example 9 Formulation Method for Reagents for Test Strips 3.66 ml of DI water is measured into a 20 ml beaker and 1.25 mL of TAPSO buffer pH 7.5 (which has been adjusted to this pH using the cation of choice according to the method of Example 8) is added followed by 90 uL of a 5% solution of Zwittergent 312. 5 mg of bis-4,4-dimethylbipyridylosmium(II)picolinate chloride is added and 5 millimoles of the desired ferricyanide salt is weighed out and added to the solution which is then stirred for 5 mins. 135 mg of glucose oxidase (*Aspergillus niger*, supplied by BBI Enzymes, Catalogue No. GO3A) is weighed out and added carefully to the slowly stirred solution, which is left to stir gently for a further 5 mins. The solution is filtered through a 5 urn filter into an opaque black plastic sample tube with a screw-top lid. The pH is checked and acidifed to pH 7.5 using small amounts of 1 M HCl if found to be too alkaline.

Example 10 Test Strip Construction

A glucose sensor was made as a disposable test strip where the sample chamber is formed from two palladium electrodes, 1.5×2 0 mm held facing each other by an adhesive spacer 0.085 mm thick to form a conduction cell. The sample chamber had a nominal volume of 255 nl. 300 nl of reagent solution from Example 9 was introduced into the sample chamber during construction and dried.

Example 11 Analyte Measurements Using Test Strips

Glucose solutions of different concentrations in phosphate-buffered saline solution were introduced into the test strips of example 10. A potential of 300 mV was applied to the electrodes. The application of potential is triggered by introduction of sample between the electrodes.

The stable steady-state current that occurs 5 seconds after applying the potential was measured.

Test strips were subject to accelerated aging conditions for period of up to 14 days at 50° C. in a desiccator. FIG. 4 shows measured current as a function of glucose concentration for a test strip made using a dry reagent containing glucose oxidase, potassium ferricyanide and Os(dmbpy)$_2$PicCl after various periods of accelerated again. FIG. 5 shows the results of the same experiment in test strips that contain TMA ferri in place of potassium ferricyanide.

Example 12 Baseline Measurements Using Test Strips

Conversion of ferricyanide to ferrocyanide can result in baseline rises because inter-conversion of the two ions can occur even in the absence of any initial analyte in the sample. The susceptibility of a formulation to baseline rises is often slight. However, with a shelf life of two or more years, even a slight inclination to a rising baseline can result in dramatic shifts in sensor performance over the course the sensor lifetime. To be able to assess the susceptibility of a formulation to baseline rises it is therefore important to have a method of accelerating the rate of baseline rise. Such accelerated aging is often achieved by placing the stored sensors in a raised-temperature environment.

The change in strip baselines on aging is shown in FIG. 6 which presents data collected from sensors made with reagents prepared with a range of cations as in Example 9. The change in baseline between day 0 and day 14 found in these formulations is shown in FIG. 7 as a function of solubility of the ferricyanide salt. As can be seen in FIG. 7, all salts with solubility that is lower than the potassium salt have improved baseline stability, while salts with higher solubility have worse baseline stability. This demonstrates the utility of solubility as a way of selecting a suitable ferricyanide for giving a low baseline rise in a formulation, as well as showing the impact on baselines that such formulations have.

Example 13 Effect of Buffering Agent on Reagent Stability

Studies have been done to identify simple organic compounds that provide a hydrophilic environment to limit enzyme instability, and for stabilizing glucose oxidase in the presence of potassium ferricyanide, alanine anhydride has been found particularly suitable by the present inventors. However, in changing to tetramethylammonium ferricyanide, this has had to be reviewed. The TMA$^+$ ion provides a less ionic environment than K$^+$ and it has been found by the inventors that simple hydrophilic stabilizers provide less stability than before. The stability can be improved by increasing the ionic nature of the reagent, but the need to avoid alkaline metal cations limits the choices. A series of Zwitterions have proved effective, presumably because these increase the ionic nature of the reagent without introducing extra free cations.

The inventors have determined that presence of a buffer in the reagent that has good buffering capacity between pH 7 and 8 and is Zwitterionic in nature would help with overall reagent stability. These two properties describe a range of buffers first identified for stabilizing biochemical reactions by Good et al (N. E. Good, G. D. Winget, W. Winter, T. N. Connolly, S. Izawa, and R. M. M. Singh, Biochemistry, 1966, 5, 467-477). Two "Goods buffers" that have proved their worth as enzyme stabilizers in the dried reagent are TAPSO and TES.

To test the effectiveness of TMA-TAPSO and TMA-TES in maintaining enzyme stability in a dry reagent, a series of reagent formulations were made up with 27 mg/ml Glucose Oxidase, 1 mg/ml Os(dmbpy)$_2$PicCl, 100 mM TMAferri, 2.6 mg/ml Surfactant 10G and a buffer/stabilizer as set forth in Table 3. Strips were made with each of the formulations that were similar to those of Example 10 but which employed gold electrodes and these were aged for up to 40 days at 50° C.

Figure 12:
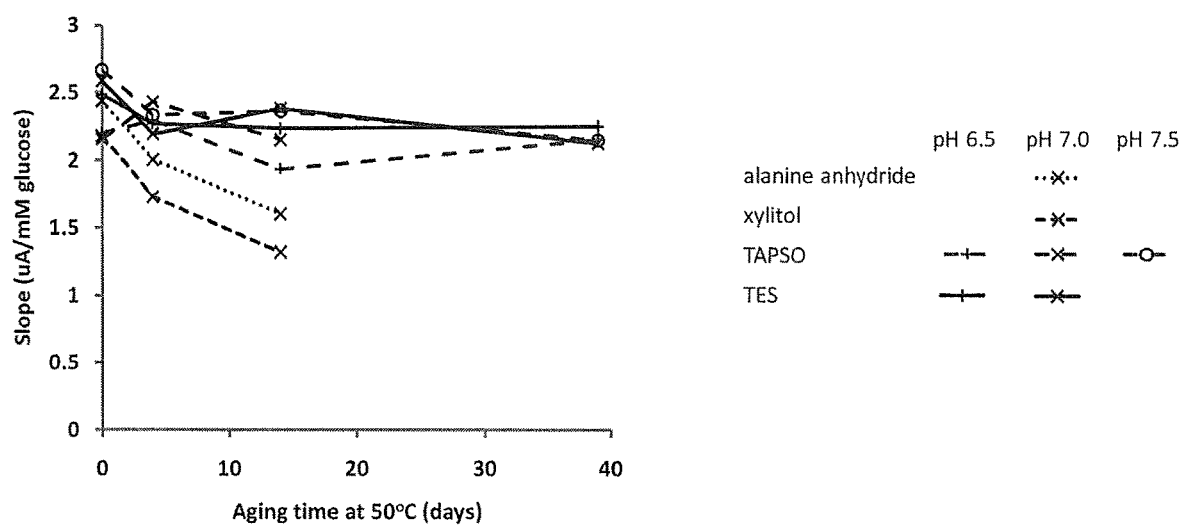
FIG. 12 shows the effect of various buffer types on enzyme stability in TMA ferri containing dry reagents.
Figure 13:
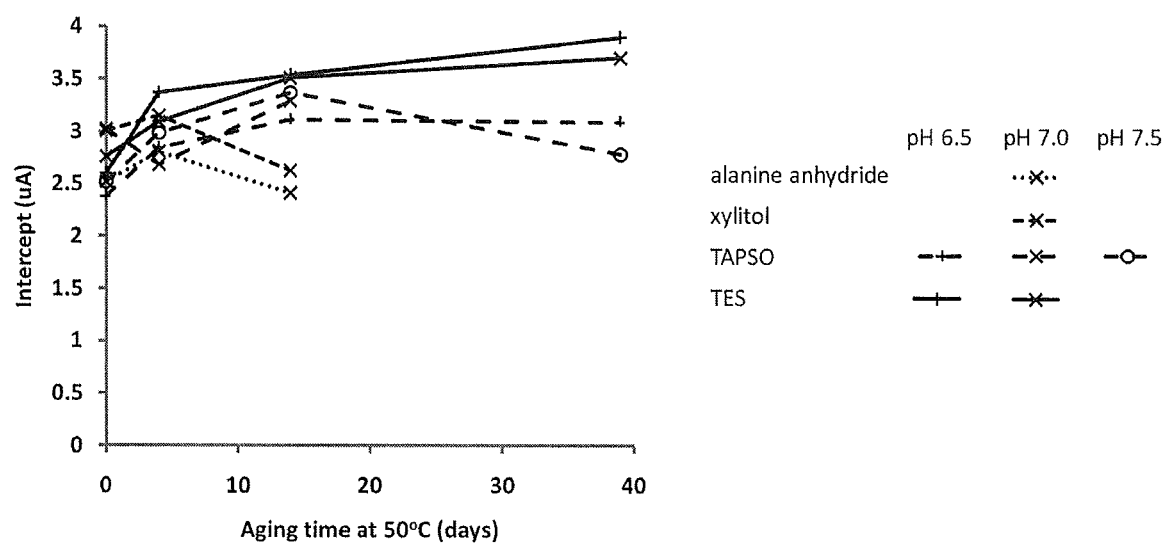
FIG. 13 shows effect of various buffer types on baseline current.

Since loss of enzyme activity results in a change in the slope of the calibration curve (signal versus glucose concentration), strips were removed periodically throughout the aging process and used to generate calibration curves. The change in the slope of the calibration curve as a result of aging was determined. Table 3 includes a numerical value for the amount of slope change at 14 days of aging. FIG. 12 shows the slopes in graphical format and FIG. 13 shows the intercept. TMA-TAPSO is superior to TMA-TES, and both are far superior to the comparison stabilizers.

Example 14 Minimum Enzyme Amount

Figure 14:
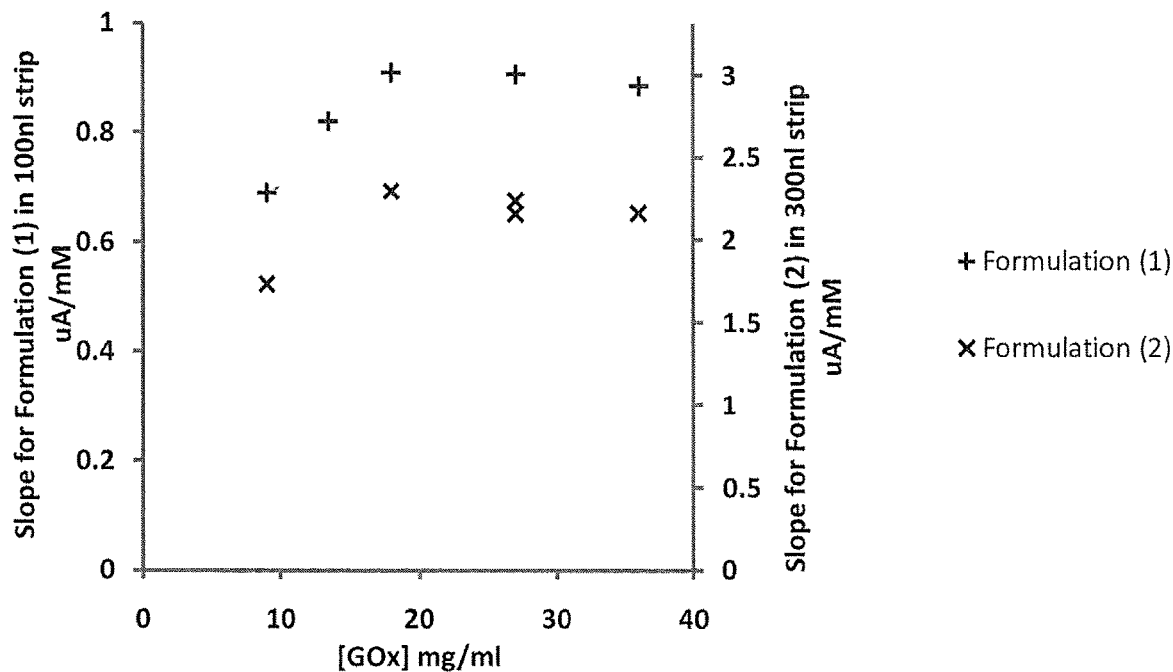
FIG. 14 demonstrates the minimum amount of active enzyme required for a stable assay.

Two base formulations were prepared as follows: (1) 100 mM KFerri, 100 mM potassium phosphate pH 6.2, 1 mg/ml OzPic, 2.6 mg/ml Surfactant 10 G, 50 mM alanine anhydride, 1 wt % silica dispersion; (2) 100 mM TMAFerri, 100 mM TAPSO pH 7.5, 1 mg/ml OzPic, 0.9 mg/ml Zwittergent 312. Varying amount of glucose oxidase were added to each base formulation and the final formulations were incorporated into test strips that were similar to those of Example 10 but which used gold electrodes. Glucose containing samples were evaluated in the test strips. FIG. 14 shows the dependence of the slope of current versus glucose concentration (essentially a calibration curve) on glucose oxidase concentration.

These two formulations are quite different and yet both show the same general form of reaching a plateau in slope by about 18 mg/ml GOx. This is therefore the minimum amount of active enzyme required for stable performance and excess must be added to compensate for activity lost over the course of the strip lifetime.

Figure 15:
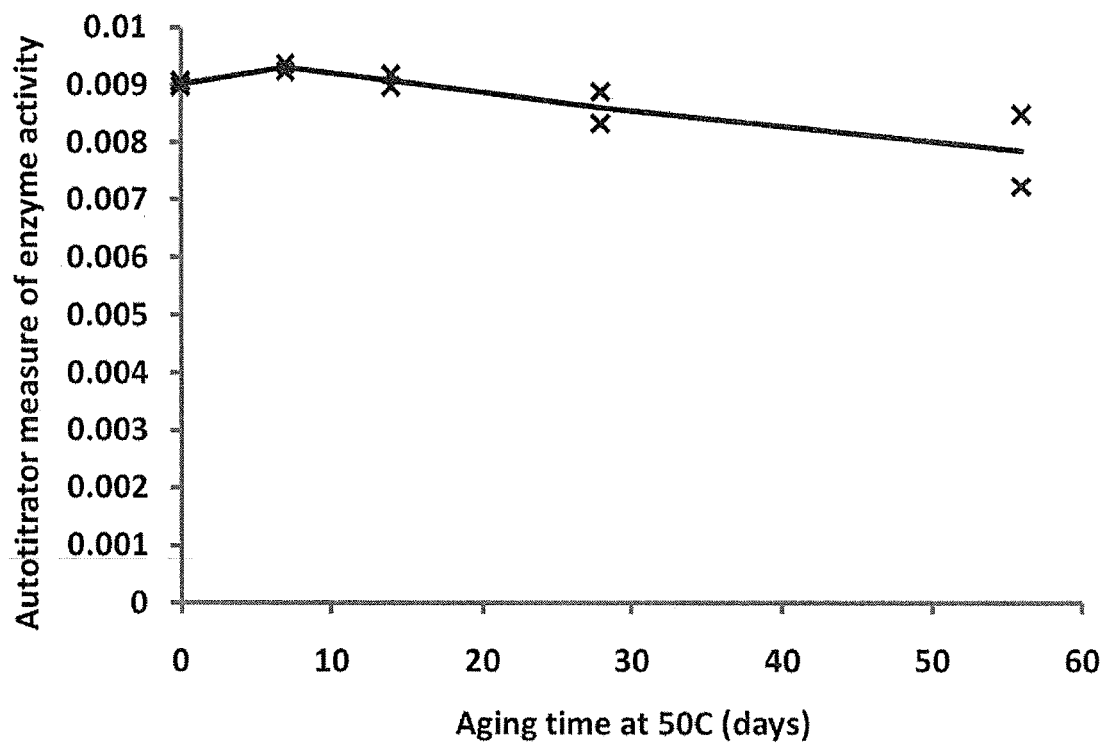
FIG. 15 demonstrates the stability of enzyme activity in a test strip containing a reagent in accordance with the invention during accelerated aging.

The amount of active enzyme in a single strip is a difficult thing to measure but it is possible using an autotitrator to monitor the rate of acid produced by the enzyme as a relative measure of the enzyme activity. A graph of how this measure of enzyme activity changes over time for strips held in desiccators vials at 50° C. is shown in FIG. 15. The reagent in the strips contained 100 mM TMAferri, 1 mg/ml OzPic, 27 mg/ml GOx 100 mM TAPSO pH 7.5 and 2.6 mg/ml Surfactant 10 G.

The susceptibility to testing conditions provides a degree of uncertainty to the readings but it is probable that the loss of enzyme activity is extremely limited over the storage period. The period investigated in FIG. 16 of 56 days at 50° C. can be equated to an equivalent time at the typical upper storage temperature of 30° C. using a factor of eleven, which suggests this accelerated-aging period is equivalent to a real shelf life of over 1 year and 8 months without significant loss of enzyme activity. Due consideration, however, must be made of the uncertainty in estimating the actual shelf life.

Accordingly, to account for up to 25% enzyme loss as a consequence of aging on the shelf, and manufacturing variations in the amount of enzyme actually dispensed to a test strip, it is desirable to configure test strips with sufficient enzyme to result in an initial concentration of at least 27 mg/ml when the enzyme is dissolved in the maximum volume of the sample chamber.

Figure 16:
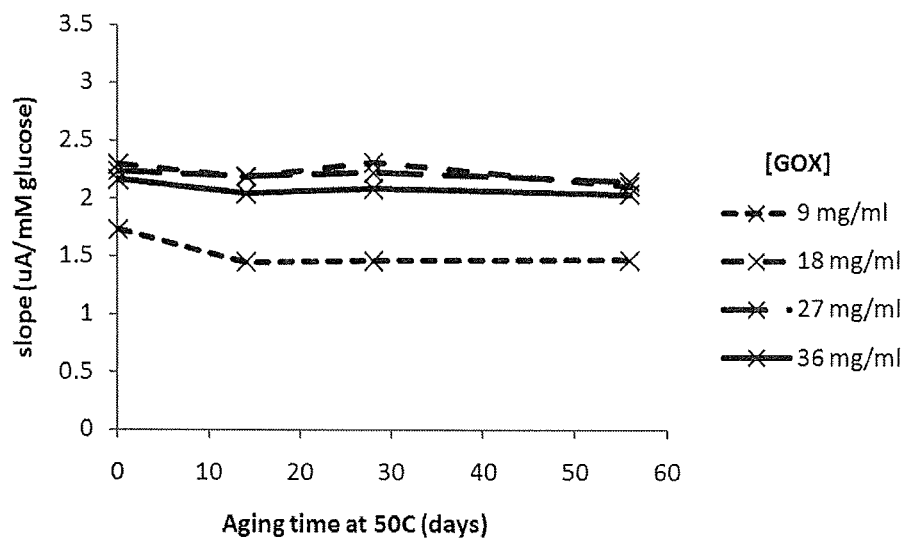
FIGS. 16 and 17 show the stability and consistency of slope and baseline in test strips made with amounts of enzyme above a preferred threshold.
Figure 17:
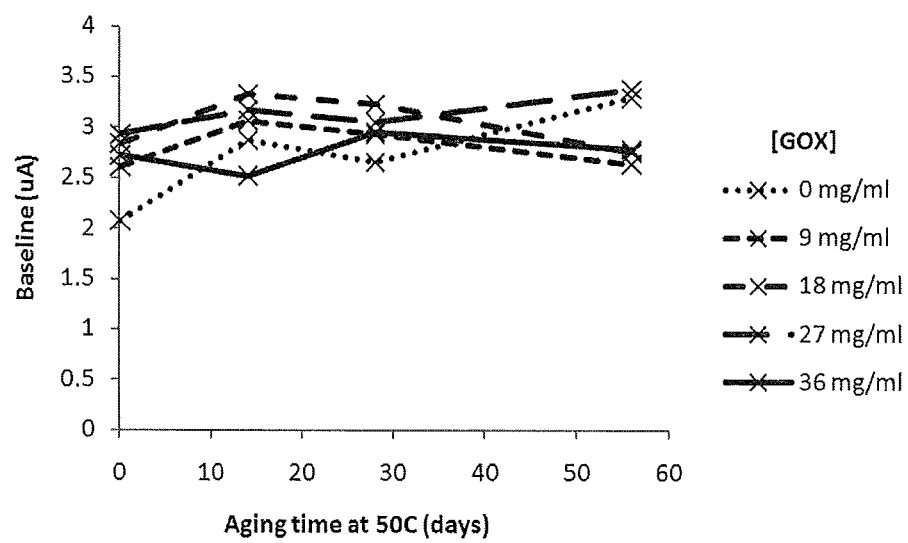

For formulations above this minimum there is no evolution in slope or intercept on aging, as shown in FIGS. 16 and 17, and all slopes and baselines for enzyme concentrations above this minimum overlap, suggesting excess enzyme does not modify the strip performance, at least at the concentrations investigated here.

Example 15 Effect of Degree of Oxidation in Wet Reagent on Baseline of Dry Reagent A batch of strips was made as in example 10 using a reagent like the one of Example 9, and so the reagent contained 1 mg/mL of the mediator bis-4,4-dimethylbipyridyl-osmium(II)picolinate chloride; the solution potential as measured by an ORP electrode was 308 mV vs Ag/AgCl. Three other batches of strips were made, the first using a portion of the same reagent but oxidizing it by stirring with $PbO_2$ until the electrode potential rose to 384 mV. A second reagent was made that was similar to the first, except it contained only 0.7 mg/mL of the mediator and its solution potential was 314 mV vs Ag/AgCl and a portion of this was oxidized with $PbO_2$ until the electrode potential rose to 390 mV; the two remaining batches of strips used these two reagents. The strips were aged in desiccator vials at 50° C. and the progress of the baseline signal was followed by periodic testing (at day 0, 28 and 56); results are shown in FIG. 8.

TABLE 1

| Analyte | Enzyme |
| --- | --- |
| Glucose | Glucose Oxidase, Glucose dehydrogenases |
| Urea (BUN) | Urease |
| Creatinine | Creatinase |
| Uric Acid | Uricase |
| Cholesterol | Cholestrol oxidase |
| Lactic Acid/Pyruvic Acid | Lactate dehydrogenase (LDH) |

TABLE 2

| Cation present | $E^0_{eff}$ vs Ag/AgCl at 0.1M [ferri] + [ferro] | Solubility at room temperature |
| --- | --- | --- |
| Sodium | 238 | 1.31M |
| Potassium | 228 | 1.09M |
| Rubidium | 248 | 1.05M |
| Cesium | 255 | 1.40M |
| TMA | 191 | 0.170M |

TABLE 3

| Formulation Name | Buffer/stabilizer | Reagent pH | Drop in slope over 14 days at 50° C. (uA/mM glucose) |
| --- | --- | --- | --- |
| Alanine anhydride pH 7.0 | 50 mM alanine anhydride | 7.0 | 0.83 |
| Xylitol pH 7.0 | 50 mM Xylitol | 7.0 | 0.86 |
| TAPSO pH 6.5 | 100 mM TAPSO | 6.5 | 0.26 |
| TAPSO pH 7.0 | 100 mM TAPSO | 7.0 | 0.00 |
| TAPSO pH 7.5 | 100 mM TAPSO | 7.5 | 0.30 |
| TES pH 6.5 | 100 mM TES | 6.5 | 0.25 |
| TES pH 7.0 | 100 mM TES | 7.0 | 0.21 |

The invention claimed is:

1. A buffer solution comprising a buffering agent formed from 3-[N-Tris(hydroxymethyl)methylamino]-2-hydroxypropanesulfonic Acid, and the tetramethylammonium salt of the conjugate base of 3-[N-Tris(hydroxymethyl)methylamino]-2-hydroxypropanesulfonic Acid.

2. A method of forming a liquid composition comprising the steps of combining an aqueous liquid carrier and a dry reagent composition comprising:
    (a) an active redox enzyme that oxidizes an analyte as a specific substrate to produce an inactive reduced form of the enzyme; and
    (b) tris-tetramethylammonium ferricyanide,
thereby forming a liquid composition.

3. The method of claim 2, wherein the aqueous liquid carrier is selected from the group consisting of blood, interstitial fluid and urine.

4. A liquid composition formed from an aqueous liquid carrier and a dry reagent composition comprising:
    (a) an active redox enzyme that oxidizes an analyte as a specific substrate to produce an inactive reduced form of the enzyme; and
    (b) tris-tetramethylammonium ferricyanide.

5. The liquid composition of claim 4, wherein the aqueous liquid carrier is selected from the group consisting of blood, interstitial fluid and urine.

6. The liquid composition of claim 4, wherein the dry reagent further comprises an electron transfer mediator in oxidized form that is not a salt of ferricyanide, said oxidized form of electron transfer mediator having an electrochemical potential in aqueous medium sufficient to oxidize the inactive reduced form of the enzyme to regenerate active redox enzyme.

7. The liquid composition of claim 6, wherein the oxidized form of the electron transfer mediator is an osmium coordination complex.

8. The liquid composition of claim 7, wherein the osmium coordination complex is selected from the group consisting of: $Os(dmbpy)_2Im_2Cl$; and $Os(dmbpy)_2$ PicCl.

9. The liquid composition of claim 6, further comprising a reduced form of the electron transfer mediator, wherein the amount of said reduced form of the electron transfer mediator relative to the oxidized form of the electron transfer mediator is such that a solution of the reagent has a baseline comparable to a steady-state baseline signal that is produced by a solution of an dry reagent in the absence of the reduced form of the electron transfer mediator that has been aged in a dessicator for 14 days at 50° C.

10. The liquid composition of claim 6, further comprising tetra-tetramethylammonium ferrocyanide, wherein the amount of ferrocyanide relative to ferricyanide is such that a solution of dry reagent with the tetra-tetramethylammonium ferrocyanide has a baseline comparable to a steady-state baseline signal that is produced by a solution of an dry reagent containing just the ferricyanide and enzyme components of the dry reagent that has been aged in a dessicator for 14 days at 50° C.

11. The liquid composition of claim 4, further comprising a zwitterion buffering agent comprising a positively-charged buffer counter ion and a buffer conjugate base.

12. The liquid composition of claim 11, wherein essentially all of the positively-charged buffer counter ion is tetramethylammonium.

13. The liquid composition of claim 12, wherein the buffer conjugate base is selected from the group consisting of: the conjugate base of 3-[N-Tris(hydroxymethyl)methylamino]-2-hydroxypropanesulfonic acid; and the conjugate base of N-Tris(hydroxy-methyl)methyl-2-aminoethanesulfonic acid.

14. The liquid composition of claim 4, further comprising a zwitterionic wetting agent comprising a hydrophilic head group including an amine and a sulphonate, and a hydrophobic aliphatic tail of 10 to 16 carbon atoms.

15. The liquid composition of claim 14, wherein the hydrophobic tail of the zwitterionic wetting agent is a 12 carbon atom tail.

16. The liquid composition of claim 4, wherein the active redox enzyme is glucose oxidase.

\* \* \* \* \*